United States Patent
Skory et al.

(10) Patent No.: US 10,351,889 B2
(45) Date of Patent: Jul. 16, 2019

(54) **METHODS AND STRAINS FOR PRODUCING BIOPRODUCTS IN *AUREOBASIDIUM PULLULANS***

(71) Applicant: The United States of America, as represented by the Secretary of Agriculture, Washington, DC (US)

(72) Inventors: Christopher D. Skory, Washington, IL (US); Timothy D. Leathers, Dunla (IL); Neil P Price, Edelstein, IL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 120 days.

(21) Appl. No.: 15/212,471

(22) Filed: Jul. 18, 2016

(65) Prior Publication Data

US 2017/0016039 A1    Jan. 19, 2017

Related U.S. Application Data

(60) Provisional application No. 62/193,875, filed on Jul. 17, 2015.

(51) Int. Cl.
| | | |
|---|---|---|
| *C12N 9/10* | (2006.01) | |
| *C12P 7/64* | (2006.01) | |
| *C12P 19/10* | (2006.01) | |
| *C12N 1/14* | (2006.01) | |
| *C07H 21/04* | (2006.01) | |

(Continued)

(52) U.S. Cl.
CPC ............... *C12P 19/24* (2013.01); *C12N 1/16* (2013.01); *C12N 9/0006* (2013.01); *C12N 9/1029* (2013.01); *C12N 9/1205* (2013.01); *C12N 9/90* (2013.01); *C12P 7/6409* (2013.01);

*C12P 17/06* (2013.01); *C12P 19/02* (2013.01); *C12P 19/10* (2013.01); *C12Y 101/01037* (2013.01);

(Continued)

(58) Field of Classification Search
None
See application file for complete search history.

(56) References Cited

U.S. PATENT DOCUMENTS

| | | |
|---|---|---|
| 5,019,514 A | 5/1991 | Bock et al. |
| 6,534,286 B1 | 3/2003 | Li et al. |
| 8,642,794 B1 | 2/2014 | Kim et al. |

FOREIGN PATENT DOCUMENTS

EP    0538049 B1    1/1998

OTHER PUBLICATIONS

Leathers. Medium optimization for production of anti-streptococcal liamocins by Aureobasidium pullulans. Biocatalysis and Agricultural Biotechnology 13 (2018) 53-57.*

(Continued)

*Primary Examiner* — Yong D Pak
(74) *Attorney, Agent, or Firm* — John D. Fado; Mark D. McNemar

(57) ABSTRACT

The present disclosure provides methods for producing bioproducts from novel genetically altered strains of *Aureobasidium pullulans*. Methods and materials for the construction of these strains, examination of the bioproducts and analysis and isolation of the bioproducts from genetically altered strains is provided. Genetically altered *A. pullulans* strains in which one or more genes encoding biosynthetic enzymes are knocked out is detailed and the benefits of using such strains described.

6 Claims, 13 Drawing Sheets
(2 of 13 Drawing Sheet(s) Filed in Color)
Specification includes a Sequence Listing.

(51) Int. Cl.
- C12P 19/24 (2006.01)
- C12P 17/06 (2006.01)
- C12N 9/04 (2006.01)
- C12N 9/90 (2006.01)
- C12N 9/12 (2006.01)
- C12P 19/02 (2006.01)
- C12N 1/16 (2006.01)

(52) U.S. Cl.
CPC ............... C12Y 207/01037 (2013.01); C12Y 503/04001 (2013.01)

(56) References Cited

OTHER PUBLICATIONS

Price et al., "Structural characterization of novel extracellular liamocins (mannitol oils) produced by Aureobasidium pullulans strain NRRL 50380," Carbohydrate Research, (2013), 370:24-32.

Li et al., "Production of pigment-free pullulan by swollen cell in Aureobasidium pullulans NG which cell differentiation was affected by pH and nutrition," Appl Microbiol Biotechnol, (2009), 84:293-300.

Mishra et al., "A Study on Downstream Processing for the production of Pullulan by Aureobasidium pullulans-SB-01 from the Fermentation broth," Research Journal of Recent Sciences, (2013), 2:16-19.

Singh et al., "Pullulan: Microbial sources, production and applications," Science Direct: Carbohydrate Polymers, (2008), 73:515-531.

Leathers et al., "Biotechnological production and applications of pullulan," Appl Microbiol Biotechnol, (2003), 62:468-473.

Wang et al. "Evaluation of single cell oil from Aureobasidium pullulans var.melanogenum P10 isolated from mangrove ecosystems for biodieselproduction," Process Biochemistry, (2014), 49:725-731.

Kim et al., "A Novel Biosurfactant Produced byAureobasidium pullulans L3-GPY from a Tiger Lily Wild Flower, Lilium lancifolium Thunb.," PLOS One: Research Article, (2015), 10(4):1-12.

Slepecky et al., "Phenotypic plasticity in fungi: a review with observations on Aureobasidium pullulans," Mycologia, (2009), 101(6): 823-832.

Manitchotpist et al., "Heavy oils produced by Aureobasidium pullulans," Biotechnol Lett (2011), 33:1151-1157.

Zheng et al., "Effects of melanin on the accumulation of exopolysaccharides by Aureobasidium pullulans grown on nitrate," ScienceDirect: Bioresource Technology, (2008), 99:7480-7486.

Liu et al., "Heavy oils, principally long-chain n-alkanes secreted by Aureobasidium pullulans var. melanogenum strain P5 isolated from mangrove system," J Ind Microbiol Biotechnol, (2014), 41:1329-1337.

Moubasher et al., "Pullulan production from Aureobsidium pullulans by continuous culture," Basic Research Journal of Microbiology, (2014), 1(6): 11-15.

Wang et al., "Agrobacterium-meditated gene disruption using split-marker in *Grosmannia clavigera*, a mountain pine beetle associated pathogen," Curr Genet, (2010), 56:297-307.

Manitchotpisit et al., "Aureobasidium pullulans as a source of liamocins (heavy oils) with anticancer activity," World J Microbiol Biotechnol, (2014), 30:2199-2204.

\* cited by examiner

SEQUENCE LISTING

```
<160> NUMBER OF SEQ ID NOS: 62

<210> SEQ ID NO 1
<211> LENGTH: 5515
<212> TYPE: DNA
<213> ORGANISM: Aureobasidium pullulans

<400> SEQUENCE: 1
aggaatctca gagtagttgc gagacatgca catggtaaag ccaaggtgaa tcctagggtt      60
gggatagagg tgagctgcgc aaagttcaat ggaattgccc aagcattcag aagggccgtg    120
catgcaaacg acaccgtcgt cgtcctcaat ggtcctgttg tcttgtcagc cactgtgggg    180
tatatcacgt atcatggtgt tcatgcttac tttccaatgt aggacagctt gaaatcaaca    240
agattgctga cgtttaccat agctggaagc acaaggtcgt ggaggcaatc gcgagcatca    300
ggacatttgc tcatgatgtg agcctccaag ggcactcttc ggggcaggta ctcgtatgtt    360
tcgggctcat catccatcaa ccccaacacc acgaggcctc caagtggcag aaggaagatg    420
gtgataatca agatacagaa ggcagcaatg gtgatgcgac cgcgagttgt gcgagaccat    480
gcacgctcat actcgcgtct tgctgtaaag aggtcttggg cagcagcttg aaggttcgca    540
cgggcttcgt tccatcttga acgaaggtct tcaagcgtgg gcttaggctg gtcctcaata    600
agaggctgtt tctcaatttc tgacatgata attcaataag ccgatgatga gcaggtgggg    660
aggataggca gatctcagag tgagtggagc atgttgataa taaaggaacc tacttcgcca    720
ctcaaaggag gctgaagcgg agcggctcag ccctacagac gtcattttta ccctgatgaa    780
cgcgtttcct gtctgtcacc ctggccatat tattttctg gcattttcc tgtatcgctt    840 cttgagacct tgaaggattt ctaggttgct ttagctactc ggagtagttc cgaggactgt    900
tctttgtata tgtgacttca actccgtgat ctttggttat agacaactaa ccacgtttct    960
ggtgaatatg gtctaccgac tgaaagaatc tctatgttga gctcgcgacg ttctcagcaa   1020
aatccataac ttagcaagca acttcaccac tccatctacc gctccatcta ccgttgctaa   1080 catacettet tegtccacta agttgcatac tgcttagtct ttcgccatcc cttgtgcagt   1140
ctagtctatc actttgagga ttgctttgtc taccgcttcg tctaccaccc agtgtaccaa   1200
tcacgttctc aacgtgctgt atacattgta ttaatagctt ttgcggagac aacgtcatac   1260
agaccctgtt tttctgtcca ttgttctcgg tcggtttccc tcaccacttg agagacttga   1320
gttttcttat gaattttcct tgtgggccaa caaacccttg ctcgtttgta ataccctccg   1380
tggtgtaccg atagctgagg ctcgcagaaa tggtgtcatg caagatgcaa gcatggagtg   1440
tgatccgaac tcttgagatc tgcagcccctt cgagttcaga gaaatattta ccaggatctg   1500
cggagccaac acccagatag ataaacccac cagacacgga tgtgcgcatt cagctgagga   1560
ctgcacatcc cttctgctgt cttgatattc catacaccag caactgcgca gcggtccgga   1620
attaaaccag ttttcatcta ataatccttg ctgctgcaga ttgtcattat tttgctcctg   1680
```

```
atatagcttc aatgtggaaa taatgtatgc aggatatctc ggggggcccc tggaggctga    1740
ggtcggagct cgcggttctg gcggttggac cttttttgga gctccacccg acagcgtcat    1800
cccggattta ttgttgacct ggccataatc gtcactaggt ggctacatcc actcaacaga    1860
cccttgctcg aaaagcaaag tcaaggaaga gctgagcgaa aagatcttcg cagtccgaac    1920
atcttccgcg tagctacata attagctttc tctcttgcaa ctcgtctctt ctcaattatt    1980
tttctgtaca gcgagacatc atgcctcact ctacatcaca gtctttcaag ctgataagca    2040
agaacctctc gcagatcgcg tcccagtcgg gtcgcgcaac tgtgagagtg cccacctatg    2100
accgttcttc ggtcaaggag ggcgtcgtcc acattggtgt cggtggcttc cacagagctc    2160
acttggccgt gtacctccac aacttgatgg agaagcatgg tgtgcgcgac tatgccattg    2220
ctggtgttgg tcttcagcct ttcgacgctt ctatgcgcga catcctgaag aagcaggacc    2280
acctttacac tgtcattgag cgtggtgccg atggcagctc tgccaacgtc aatggtgcca    2340
tcacctcgtt cctctttgcg cccgacaacc gcgaggctgt cattgcgaag atggctcacc    2400
ccgacaccaa gatcgtttcc atgaccatca ctgaatccgg ctactactac aacgagaaca    2460
ctcacgagct tcaggctgag cacccccgaca tccagcacga tctcaagaac gagaactcgc    2520
ccaagaccac cttcggtttc ctctacgccg gcatgaagac acgtcaccag ctcggtctca    2580
accccttcac tgtcctctcc tgcgacaaca tgcagaagaa cggttccatc acacgtcaca    2640
tgctcgtctc ctttgccaaa ctcgccaacc ccgaaatcgc caactggatc tccgagaggg    2700
gtgccttccc caactctatg gtcgaccgta tcactccccg caccgaaaag accgacattg    2760
ccgcactcgc cgaagacttt ggtattgagg atgaatggcc agttgttacc gagcccttca    2820
tgcaatgggt tgttgaggac aagttctctg acggccgccc tcccttcgag aaggtcggtg    2880
ttcaggtcgt caaggatgtc cacgacgtcg agcaattcga aatgcacaag ctgcgtctcc    2940
tcaacggttc tcactctgct ctcggttacg ctggtcagct cgctggtttc aagtacatcc    3000
acgaggttat caacgaccct gtctaccgca gtttgtcga gcagatgatg cacaaggaag    3060
tcaagcctct tctgcccaac atccctggtg tcgacattga ccagtactgc aacaccctga    3120
tggagcgttt ctcaaaccct accatcatgg atcagcttcc tcgtatctgt ctgggcgcct    3180
ctggcaagat ccctcaattc attatgcctt ccatcgcaga gcagatctgg ggtgagcaca    3240
acttccgccg tctctgtttc gtcgctgctg cctggttccg ctacatcaac ggtgtcgatg    3300
acgctggcaa caagttcgtc gtcgacgacc ccatggtcga ggagctccag gccaaggcca    3360
aggctggtgg cctcaagcct cacgagcttc tgagcatcaa gtccctcttc ggtgacgact    3420
tgcgcaacga cgagagattc gtcaaggagg tgactaccgc tatggagctt atcgccaagg    3480
acggtgtcat ggccactctc cccaagtacg ttgactaagc gattgtcaat gtgtgttgaa    3540
gggagagctg ctggtcggct tgtcccgtca cataatacag aaagagaagg agtcaggata    3600
caaatacctt ttatcataca agaacacgct tcgatttgcg caatcgcgca tgaggacacg    3660
acgagccaaa gctctgagat ataatatacc cccgagctcg cgggttcacg aagagaagcg    3720
agttgacttg taggatagac atggattggt tatagaccac atttagatga ttcacagcat    3780
atttgaagcg atttttttgc cagtctcccg ccctctgatt cagtgtgctc ttggacgtga    3840
tgatctgatc cgaagcaagc ataatatctc ttgccttgtc ctcagcctct ggcatgtttt    3900
cagactaagt tgtaatggtc agatgctgtg tattgcttgc tcgactcgac aacgacctcg    3960
agactgtttg aggagagcct gcacatgacg atgcgcgttg cggagatgac ggaattggtg    4020
gcttgtgcct cggaagtgca cgcgagtcag cgaagtcacc aggctcaaga tacagtcatt    4080
```

```
cgccatggcg tcgtccgctc tttgacccta caccgactgt cctctggaaa cagaggaagt    4140
aaatacaaga catggccggt caaggaagcg gaaatgctgg tcgaggggg actgttattg     4200 acaaattgga ctaccaccct ggacgaccgc tattacgtgc cgacgacgaa ggggaatcat    4260
caggcagacc cagtgccgag cacagttatg ccggcagctt cttttgagcag gtcgccgagg  4320 gcatccagaa ccgtgataga cagaagatgc agcgtcagct ctcgcgttat ctcacctttg   4380
cctgggccat tgtcaactgg tccgttctcc atctagcctg aacagagcat gactgataca   4440
tcactctagt ctggttgccg gatccatcac ctgcttctcc gtatacgctc ccttgttcca   4500
gaaacgtttg cactacaccc agctgcgcgt caataccatt tccatcaccg ccagttgggg   4560
catgtacttg cctgtgccta tctttggctt cctctgcgat cgctatggcc ctggcattcc   4620
ttcaatcctg tcaggctgtt tcgctggctt tggctacata ctagcagcct tcacttaccg   4680
caatcccgac tggccttcg ctgtaatggt cttctctttc gtttgggtcg gcatggctac    4740
cagctgcatg tatctcagtg ccgtcaccac ttgcgcaaag aactttggaa gaggaaaaca   4800
caagggcctt gcactagctc tacccattgc cgcttttggc ttgagcggta tgtgggagag   4860
ccaggtggga agtcgtctgc tatacgaaaa gaagcctgac ggcactcctg agacattga    4920 tgtctttcgc ttttttatct tcctcggatg cactctattc tcagctggtg ctattggctt   4980
tttcctgctg aggatcatcg atgaggacga gatgattgat gaagcgattg aagagctgga   5040
acaaagcggt ctgttggagg acagtgcttt ctttagaaga ggtcaccatc acgagcatca   5100
tgatacctat ggtgctgtgc aagacgagga cgacgaagaa gagcgtcaac gcaaagaaga   5160
ggaagaagcc cgcaagaaga catggctact aaacgaggag actagccgct tcctttctga   5220
caggaccatg tggctgctcg ctggtggatt cttccttgtt actggtccag gcgaggcttt   5280
cataaacaac ctcggcacag tcattggcac tctataccccg cccaatgttc ctgatgagga   5340
tattcctaca agcgctgcta cgcacgtctc gatcgttgct attacctcaa ccatcgcgcg   5400
tatactgaca ggcaccttgt ctgacttgtt tgctcctacg tctgttccac accagcatcg   5460
tagaggcccg aactcgctcg tatcatccat ggccaccttg cctggtacag acgct         5515
```

<210> SEQ ID NO 2
<211> LENGTH: 4801
<212> TYPE: DNA
<213> ORGANISM: Aureobasidium pullulans

<400> SEQUENCE: 2

```
attacgaaga agatataggt tcatggatga gagacatggg cattgtgttt aggaatcggg      60
ttcattccac atacatcgac actacagaaa ccgcttcaga ggctggactc cggattcttc    120
atcacacaga tgtgcctgag gggacgcaat ttgacacctg gagttacggt ctgttggtga   180
gcaaagagga tgacccaatc tctagcgttc aagactggtc tctacgaggt gctctagacg   240
gaagcctatg gtctctgcct gatgccagag cttggattt aacatggtgc tttaacgaac    300
gtggtgcaag agtcgtatag acgatttgcc gagctttaac cataggcagt taggggagtt    360
gtccatcacg tagatattga agcacattgg gtaatcgagg tggacgtcgc atgtaggagc    420
gctgccacga cttcttgtcc ttcttccttg ctctttttcta gctctggtgc ctagtcgtgg   480
caataccgtt ggttgtacta atgatggagt gttattggag ggtcttgtaa tatcgctcag   540
tcgtgaaaat tgtcgaagca tcgcgcggtt ttggttcctt cctagcaagc gaatctgatc    600
agtgtaatta agcgatggag tgttcacgct catgtcatcc acagagcgtt gtgaaccttc    660
```

```
tagagttgat acgagactta atgtatcttc ttgggtagtt ttgctcagta ataaccagga    720
ataatcgttt ggtactgacg aaccgccaaa gctctaatcg acatgtcagc gctttgaagt    780
cacctgaaat cactctgtat ctgcggtatt gcgcctgcaa cttgtgcaaa agtcaatgtc    840
acactgcttg aacacattgc gatgtgctcg cgcagggcta agtttcattg catagatgcg    900
gctgttgtcg agaactcgtg aagcgcgaga gcgaccatct gttgtacgaa aacagtggtc    960
gagctatttt tccaaccaaa aagtagggat atagtgtgtt ttcgtattca ccgccagtgg   1020
ccgcacactt gcatgatcct tcgttctgaa actttgggcc acaagaccgt tcacgtcgaa   1080
tcgtcgacac gaacccgctg acttggaatt gcgatcatgt tgccgttgca gtgccaatgt   1140
agacacgtat agcaatagta tgtggtcgtc cgatacgcgt aaccccctcc ttgtctagtg   1200
gcacccgagt gggcggagtt ggcgatagca ccgacagcat cttgaccccg ctgaagcagc   1260
tcgtctttgt tcgcaccaga gattgcagag cgaaacgata gacacagggc aaagaaaatc   1320
gtcagagcga gcatggcctt ccaccatgag cttcttgaga tttctatttt ctggcaaaac   1380
atcgacgatg atggaactaa acgatcgttg atttccagtt ttggtgaact gtttgttgtc   1440
cgtgctcaag caagaggtgt gaagatcgag gatttggcgg ggcagtgaca ccggagctgt   1500
cgggaggttt cgatcttttg gactacaagc ggaccgtgca tactgacatc acaccagggc   1560
catgtggttt tgtcccacta ttggatcatc tgaagctcct gccacgaaaa gtcttgcagc   1620
aaatcagtgc cacaaacaag tcagaattcg gccctttcag tcaacgttca gtcaagccgc   1680
aagtttgctg tgctaggggc tgcttccatg ttgttctcca tctgttgagg ctcgttgacc   1740
gggccacctt cagccccacg accccgccta tgaggtcagt gaaagaagcg tggtgaagct   1800
gcaggaccac cgaggagcac ttttggctgg atcccagcag aaaatatgac ctcagcccat   1860
cgagcggtaa gaagtggacg gatgaagctt ctttttttaaa tagctatctc ttcccctgca   1920
catctttcct ctcttcatcc tctcttcata ccaattcatc ctccttttc caccaataac   1980 ccccaccaaa tcacatcaac atgcctatct ctatccccaa gggcgagaag cttatggacc   2040
tgctctccat gaagggcaag gtcaccattg tcactggtgc ctccggtccc cgtggtatgg   2100
gtattgaggc cgctcgcggt atcgccgaga tgggcggtaa cgttgccctc acctacgctg   2160
gccgtaagga gggtggtgag aagaacgccg ccgctctcga aaggagtac ggcatcaagg   2220 ccaaggccta caagctcgac gtcgccaact acgagtcgtg ctgccagctc gtcaaggacg   2280
tcattgccga ctttggccag attgacgcct tcgtcgccaa cgccggcaag accgccgact   2340
ctggtgttct tgatggcgag atctccgcct tcgaggaggt tatccagacc gatctcctcg   2400
gtgtcgcata ctgcgccaag gctgtcggcc accacttcaa ggagcgcaag actggttctt   2460
tcgtcatcac cgcctccatg tctggtcaca tcgccaactt ccctcaggag cagacctctt   2520
acaacgtcgc caaggccggc tgcatccaca tggcccgctc cctcgccaac gagtggcgcg   2580
actttgcccg tgtcaactcc atctccccg gatacattga cactggtctt tcggactttg   2640
tcgacaagga gacccagaag ctctggcact ccatgatccc catgggccgt gacggtgacg   2700
ccaaggagct caaggctgcc tacgtctact tctgctctga cgcctccacc tacaccaccg   2760
gttccgacct cgtcattgac ggtggttact gcgcccgcta acagatcgc tggctgatct   2820 gtttgttttt ggtcaaaggc caattcacct ttcttctact atcaaaatag ttaattattg   2880
cctcatgacg gtcatgaaat gaaaatatga ttcccagtct acttctatct tcttgaactt   2940
gttcttactt tcttctattg gtgtattggc aacgcagttg gcatgctgtt cccacgactg   3000
ttgtcgcatc gtgttgactc ttgagatgca cgcgctcaca ccagtcaagt ctcagtccag   3060
```

```
gtaagaacca taacagcgac agtcgtagct gatagtacca aggatagcgt acaatcgaaa   3120 cccttteegg ctagaatcga cagcggaatt cttcacgaca accagtaaag ccgcaccctg   3180
gaccgtcata cgagcagatc gatgcaagac cttctaccgt accgccctct gtccgaatcg   3240
atagcacatc aacctggggt tcttacatcg gttgtagaac aaatcctccg acacgctcag   3300
acgtccgaga acggacagag tacagcaaat agcctaagct catatgaaaa gaggaagaaa   3360
tcaagctacc cagggacaag aaggatcaga gatggcacg aacccggaca agacgttcca    3420
agcacacaag ctctacaata tcaggtccat tgacaccgcg agcgaagcaa ttcaaaccgg   3480
ccactgtgtc aatgctctac aactgtgctg cgtccaccag agaaaatcac gcaaactcca   3540
caccatcgag gcaccaccca gccagccctt tcaacccagc aacaaaaaca cacaaagcag   3600
aagcaataat gaacatgctg atactctctc caatctcggc ccgactcccc tcgtctttta   3660
ctgcccaaaa aaatctcagc gtcaaatact cgccaacccc catgatgaca acaaacaaac   3720
tcccagctcg gaggattagt cttcgagtca gggttccaag gttagcagag accaaagcaa   3780
atggagctag gattttaagt atcaaagggg cagtttgggc gaagggtgaa aagacgggga   3840
ttagacggta cacggcgtcg agggaaaagg aagaaatgga ggcaatgttg ccggtgctga   3900
aaagagcgga ttgcagcaaa aagaggaaaa acagacagat gcgcaagtcg tacagagtga   3960
gaggtctgta gtggtcgctt gttcttattt tactttcgtt gttgggtcca gccatctcgg   4020 tgactttga tggtgctgat tttgctagtt tggtgctttt ggatctcgaa gggatggcag    4080
cgcaaactgt ggccttttgt tagcactgct ttttgtcggt tgatgtgtct ctggacgagt   4140
gtgttgccgt gtaccttcat gatggtaatg ttgctgaatc ctgtactcga gacgcaccca   4200
actaataagt gtgatagcaa aagcagcata aaaaagtcct tcatacgaga tggaaagaat   4260
aacaaacagc gggccaaaag tcaagaaaat ggctgtatga cgatagagat agtatcttct   4320
tgggcgcagg gaatgaccga aaggcaagat gaaggacgcg actgggtttt tcacacagtc   4380
gatcagtaat ggagacaata tagacaagag atcttttaga aatgggactt actcaaagtg   4440
gcccatccaa ggatctgtgt gggtttggga agtcctcgtt tggcttggag tgaggtcacg   4500
cttgacttgg tcactaacat cgcaagacca acgagtgcta cctgcaagcc aagaatgacc   4560
gttgacagag tatcgcgctc ttttgagaaa gcagaaggct ctaatagctt cttctcgaac   4620
acgatataca aaagacctag cagaaggatg ctggaaccac caatcagact gccaaaatat   4680
gagctttgcg ttctgtctga aagaaagatg ccaacataca tgagagtaag atcttctatt   4740
tttttggcta gcaatagagt aaagacgctc atagcggagc aagaaaagat ccatgttgta   4800
c                                                                  4801
```

<210> SEQ ID NO 3
<211> LENGTH: 10406
<212> TYPE: DNA
<213> ORGANISM: Aureobasidium pullulans

<400> SEQUENCE: 3

```
aatagctcgg aaacaactga cagagtattc acagctctgt ttggaagtgt cgccccttc     60 gagcacgagc cattaatcca tgaaacgcgg gtcagagtcg acttcactgt tatcgtgaag    120
gagcgcggac cactggtcgc aagggtagca agtctgagga gacacagaca cctgaagttg    180
gcactgtctc gtttcgatct cgcgcgagtt tgcattcttc tcgaatgcgc aagacgccga    240
acaaagcttg gatatggttc tgcacgctgc atgctggcga agcgagcatc gatgaggaca    300
```

```
gacagatact aggggttaaa tatggaaacc aagcgtgaaa aaagcagtcg agattgttta      360
gactgctctg acaatgctga ggaaagaacc agggtacaca aggcttgctg agtgtgaaca      420
cgattctgaa ttctgaaggc tcgagccaga acacgcaaca gtctgatgtg agatgtatat      480
acttgccatt tttttctcga gcacgacttg tagatttcca accagccagc ctgttctttg      540
gttgggtttg ctgtagaatc acaccggtgt tgctcaagat gctgtgacac gtcgagacag      600
agcaacgtgc gaagaaggtg ccgggtgcca agctgcggca agccgggcag aaaggcatga      660
atcattggat ggtgctttca aggttccgac gcgccgcgca ctgtcaaaaa ttccgtgcca      720
tattcataga accccacaaa acactggccg cctcaagttc ctctacagta cagcatcgta      780
tagcagatcc aaagcgtgtg cgctgccctc agcctggtgt tgccaatcta aatttgtcgc      840
tctgacatga tgatgcgaca tgatagaccg tactgtacct ccaacattca gctcaccata      900
ctcattggca tgaggtttct ggaacggcga tccacaatcc tgtcactgag gccagctgcg      960
atccacggcg ttagggttgg cccaaatgca caccagctgt gtcttccatg ttcaaatcgc     1020
ataatggact agtaaacctc cggtggcaat agctgtctgg cagcgggctt gacgttcacg     1080
accatgcacg ctccgcaagt atgtcggacg tgccaataat attccggacc caacagtaag     1140
tttagtggca tctttgcggt tgcaatagtc acttgctgca tgctctgcaa ccttgctgag     1200
ggcgttctct atttcggtcg atcggggcct tactggttct agcagcaaag caagggaata     1260
cggacttcga gtcgcggctc tccacacatc agatcgctgt aacccagcat cgtctcacgt     1320
ttcttatctg gtttcgactt gacgctaccc aaccgctgaa ctcagtcggg ctcgcttccc     1380
tgcgccatc aatagtatgg tcggagattc ctgcgactct gcatggcatt ctgctggtta     1440
gtctccatac cgcacgagtg gaccctctgc ggaattccgc tgttcgtaga catcactctc     1500
ctcacgtcag gaacatggat caaggctggc tgtacacgtc ccgccggctg taaggtggtc     1560
atcgtagcct cgcagtatca gtgcttcgcg aagatccgct gccggtacta gtggtctcca     1620
tacacaatcg ctcgatctta tgcgagtggt tttaccttcg acattattt gagctcccaa     1680
ctctactcga caatatatat cctcctcgtt cccaagttct gtgtctcctt ttctcattca     1740
agccatcttc ccttgttact tcgagacgtc cagcccacat ctcgagtact ctacatttcg     1800
tttcattgta tagtattact cacagccaga gtatactatc acattaatcc acccttcgtt     1860
ctccgccaca tcatattctg ttgaccctag ccaagtcatt cgaatatcga tactttcagt     1920
actatcgttc ttcaaccagt tcatccacga atcaccctaa tttatcgatt atactgcaag     1980
tcagcttcaa ttcacaacaa tgtcaaacgt tcttctttc ggcgaccaga ccgccgagca     2040
gtaccctctg ctccgcaagg tggtcctgag aaccaagaac gcccttgttc ttaacttcct     2100
ggagcgtact gtcgttgctc tgcgcggaga aattgcccaa ctctcccgcc tcagcgcga     2160
tgccattccg gatttcatga ccctcaacaa cttggtcgac ctttactacg agaagggact     2220
gaaacttcct cacctcgaga gcgccctggt cactatcgct cagcttggtc actacatcgg     2280
atactttttcc gagaacacta gcgagcttcc tcctgctgcc aacactcgca tccttgctct     2340
ctgcacagga tcgcttgccg ctgccgccgt cgcttccgcc aggactctcg atgagctcgt     2400
cactcttggt gtagagactg ttcgcatcgc cttccgcact ggtgttcgcg tcaacgaagc     2460
cagaaccgct ttgggtcagg acctcatgtc cagggagagc tggtctacta tcgttactgg     2520
catcaacgag cagtctgcca aggaggctct gaacgctttc cacgagtctg ctggcattcc     2580
caccaccagc cacgcttaca ttagcgctgt cagcacaatg gccatcacta tcagcggtcc     2640
tcccaccacc actaagcgct tctttgagga gtccgaggct gttcgcaaga acaaccgcgt     2700
```

```
caagattcct gtctacgctc cttaccatgc cgagcacctc tacagcagtg ccgatattga   2760
cgccatcatt ggcgaggagt ctgccaagct cctccaggct tatcagcctc gttcgttggt   2820
ccactccggc tcgactggca tgtgccacat tgccgagaac accttcgagc ttttcaagtt   2880
gtccctgaac gacatgctca gatctcctgt tggctggaac aacctccttg aggagagcgt   2940
ttctcagatc accgccaaca ccaatgcttc tgccaaggtc ttctgcattg tgtcagcaa    3000 cgtatctaac agcctcgtct cggccatcaa agctggcggt caatcctcgg tctccctcgt   3060
tgaccactct gcctgggagt ctgccgtcac tgatgctacc cacggtcgca cccagaacga   3120
caagattgcc atcgttggta tgtctggtcg tttccccagc gctgccagta ccgaggctct   3180
ctgggaactt ctcgagaagg gtctcgatgt tcatcgcaag attccctccg accgtttcga   3240
tgcagacgct cactgtgatc cctctggaaa gggcaagaac aagtcgcaca ctccttacgg   3300
ttgcttcatt gacgagcctg gtcttttga tcctcgcttc ttcaacatgt ctcctcgtga    3360
agctgcccag actgatccta tgggtcgtct ggcccttgtc actgcttacg aggctcttga   3420
gcaatcaggt tacgtcccta accgtacccc ctctactaag ctccaccgca ttggtacctt   3480
ctacggtcaa acctctgatg attggcgtga atcaacgct tccgagaacg ttgataccta    3540
cttcatcact ggtggtgtgc gtgcttttgc acctggtcgc atcaactact acttcaagtt   3600
cagtggtcct tcgttttcaa tcgatactgc ttgttcgtcg tctttggctg ctatccagct   3660
tgcctgcact tcgctgtggg ccggtgactg cgacaccgct tgtgctggtg gtctgaacgt   3720
cctcaccaac cctgacattt tctctggtct ttccaagggc caattcctgt caaagacagg   3780
ttcttgcaag acttacgaca cgctgctga tggttactgc cgtggtgatg ttgtggtac    3840 cgttgtcctc aagagatacg aggatgcgct ggccgacaag gacaacattc tcggatgcat   3900
tcttggcgcc gctaccaacc attctgctga ggctgtttct atcacccacc ctcacgctgg   3960
tgcccaggag ttcctttaca agaaggtcct tgccaatgct ggtgtcgatg cccatgagat   4020
cagctacgtt gagatgcacg gtacaggtac ccaggctggt gacggtattg agatgaccct   4080
ggttaccaac gtcttcgctc ctcgtcaccg tcagcgcaag cctgagcaga agctccatct   4140
cggtgccatc aaggccaaca tcggtcacgg cgaggccgct tctggtatca actctctctg   4200
caaggtcttg atgatgatga agaagaacgc cattcctgcc aacgttggta tcaagggcga   4260
gatcaacaag actttcccca aggacctgaa ggaccgcaat gtccacattc tcagcagca   4320 gattgacttc ccccgtaacg gcgctgagaa gcgcaagatc ttcctcaaca acttctccgc   4380
tgctggtggt aacactgcca tccttctcga ggatggacct ctttgtgagg ctcccaaggc   4440
tgttgacccc agaggcactc ttcccgttac tgtcactgcc cgctcgattg ctgccttgaa   4500
gaacaacatc cagcgtctgc agggatacct ccgcgagaac cctgaaacca ctctgcccag   4560
cttgtcttac acttcaactg ctcgtcgtat ccagcacaac taccgtattg ccttcccaat   4620
tggtgatatt gccaaggtta gcgatgctct tcaggcccag accaaggaca cctacagccc   4680
tgtccctatg gtccctacca agactgcctt ctgcttcacc ggacagggtt cgcagtacac   4740
tgctcttggt cagaagctct accaggacct caagtctttc cgtgacgaca ttaaccagct   4800
tgacaacatg gccaccatcc aaggtcttcc ttcgttcatc gagctgcttg acggcactga   4860
cgttgctact cttttctcctg tcaaggtcca gctgggtatg gcttgcatcc aggtcgctct   4920
cgctcgcatg tgggcttcgt ggggcgtcac tcctaccgct gtcatcggtc acagcttggg   4980
cgagtacgct gctcttcacg ttgctggtgt catctctgcc agcgatatga tcacactcgt   5040
```

```
cggtcgccgt gctgagctcc ttgtcaaaga ctgcacacct cacacacacg gcatgctcgc    5100
tgtcaagggt ggtgctgatg ctattcgtga cgttctcggc tccaagatga ccgagattgc    5160
ctgcatcaac ggcccggagg agactgtcct ttgcggtagt ggtgaggttg tcggtgctgc    5220
caatgaggct ctttccgctc gcggcttcaa ggccaccaag cttaacgttc ccttcgcctt    5280
ccactcggcc caggtcgacc ctattcttga gtctttcaag aaggttgcat cttctgtcac    5340
tttcaacaag cctgccgtcc ctgttctttc tccctgtct ggagacctca ttcgtgaggc    5400
cggtgttatt ggccctgact acctcgctag acacgccaga gagactgtca acttctggac    5460
cgctctaacc actggtcaga aggagaagat cttcgacgag aagactgctt ggcttgaggt    5520
tggcgcccac cctgtctgct cgggcatggt caaggcttcc gtcggcgcca ccattacatc    5580
cccttcgctt cgtcgcaatg aggacccctg gaagaccatc gcagccagcg tctgcgctct    5640
cttcaacgct ggcgttcaga tcaacttcga tgagtaccac cgtgagttca cgctgctca    5700
ggaacttctt cctctgccta cctactcctt cgacaacaag aagtactggc tcgactacca    5760
caacaactgg actcttacca agggtgaagc tcctcgtgag gttcagaaga ccatcgaggc    5820
cgctcctcaa gctgctcctg ccgtcgagaa gcctgccaag cgtctctcca cttcgtgcca    5880
gaaggtcgtc cacgaggagt cgaggccaa ctctggcact gttgttatcc agtccaacgt    5940
tgccgagccc aagctcttcc aggcagttat tggtcaccag gtcaacgaca ctgctctctg    6000
cccctcgtcc ctgtacgccg acatggcatt gaccgtctgc gactacctct acaagcagct    6060
cagaccctct gctcccaaga tcggcatgaa cgtttgcgag atggaggtcc ccaagccctt    6120
catcgccaag atggagcagc ctgctgaagg ccagcacatc caactcgagg ccaaggctga    6180
ccttgacgag ggtgtcgctc acctgaagtt cagaagcgtt actccggaag gcaagctcat    6240
tcaagaccat gctcactgtc tggtcaagtt cgaggacatc agctcctgga cgaggattg    6300
ggagcgtatc aacttcatgg tcaagtctca ggtcgatgtt cttaaggcta agaccaagac    6360
gcaggaggct cacgtcatgc agcgtggtat ggcctacaag ctcttcaagt gcttcgtcaa    6420
ctacaacgag aagtaccgcg gtatggaaga ggtcattgtt aacagccaga ccactgaagc    6480
tacagcttct gttaagttcc agaacggtcc cgccgatggt gactggtacc aggcccctta    6540
ccagattgac agcatgtgcc acatctcagg tttcattgtc aacgccaccg atctgattga    6600
ctccgacaac aacgtctgca tctcgcacgg ctggggttcg atgagaatcg ccaagcagtt    6660
gactcctgag ggcaactacc gctcttacgt tcgcatgctt cccaagcctg gtaacatcta    6720
ccaaggtgat gtttacatca tggagggag cgagattgtc gccgtttgcg gtggtctcaa    6780
gttccaacag atccctcgcc gtgtcctgaa cgtcttcctg cctcctcaga aggctggcgc    6840
acctgccaag gctgctgccc ctgccgctcc cgctgccgct ccaaaggcag ttgctgcccc    6900
caaggctgcc gctcctaagg ctcaggcccc caagcctgct gtcaaggctg ctaaggctcc    6960
caagaaggtc gctgcaaaga agtctcaagg cgctaccatt acttctcgtg tcatgcaaat    7020
cattgctacc gagaccgatg ttgagcagtc tgagcttgtt gacgaggctg cattcgagaa    7080
ccttggtgtt gactctctca tgtcgctgac catctctgcc aagttcagag aggaccttga    7140
catggagatc agctccaccc ttttcaccga ttaccctact gttggcgaga tgaagaagta    7200
cttctctcag ttcgatggta acgttggtcc ggttgaagat gattccgagg acgagtctga    7260
gccctcagac attgccactc cttacgagga tgacctgagc accccgcca gctctgcgcc    7320
tagcactgca cccagcgatg ctggaaagcc tgatattgac tctcctaccc gcgagattcc    7380
tgactccgaa gttggtgaag tcagcttggc tcgccacatc atcgtccagg agatgggaat    7440
```

```
tgacagctcc gagcttactg atgaagcaga cctttccgag cttggtatgg actcgttgat    7500
gagcttgact attctcagtg aacttcgcga gaagaccggt attgatcttc cctcgacctt    7560
cctctctacc aactctacca tcttggacat tgagaatgct ctcggtatgc gcccaaagcc    7620
caaggccaag gctgctgctg ccccaaaggc cgcaaagcag acctcgcctc aactcgacaa    7680
agtcaacgca aagcttaccg atctttccaa gtatcccgcg gcaacctcag tcctcctcca    7740
gggcaatgct aagattgcta ccaagaagat tttttttcctg cccgatggtt ccggctctgc    7800
tacatcctat gtcagcatcc ctaacatcgg ccctgatgtc gctgcctttg gacttaactg    7860 cccccttcatg aagagcccta ccgactggac atgtggtatc gagaccgtct cgctcctcta    7920
ccttgctgag attaagagac gccagcctca aggcccttac atcattggtg gatggtctgc    7980
tggtggtgtc attgcttatg ccgttgctca ggccctgctt gccaacggtg aagaagtcga    8040
gcgtctgctc ctcctcgact ccccttgccc tgtcaacctt gcacctcttc ctcaacgcct    8100
ccacgtcttc ttcaacgaga ttggtctcct tggtactggt gacccgtcca agactcccaa    8160
gtggttgctc cctcacttca gtgccgccat tcgttcgctc tctgactacg agcctcaacc    8220
ttcgttgaag cctatcaaga cctacgctat ctggtgccgt gacggtgtcg ctggtaaccc    8280
cggtgaccct cgccctcccc cagctgagga agaggaccct gcacccatga gtggctgtt    8340 gaaccaccgc actgactttg ctgacaacgg ttgggctcag ctttgcggca atgagatgaa    8400
gttcggtgtc atgggcggca atcacttcac catgatgaag gagcctcatg cacaagaact    8460
gggcaagctc atccaagaag gtcttcagat ctaaacaaac caaaaattca aaaaaaagca    8520
gcgggagggt gctcatgcta ggatgctgag aggcagtgat cgccttgggc tgaggtcggt    8580
tgcgactccc acaccctatc cttgagaaga ggtggacatt actacgaagt gatcgatatg    8640
gcttttgctt gggctgagtg aaagcccttat tgctgactct tgtttcttgt tctctctatt    8700
cactcttccg ccgtatgtgg cttctttttt tcctgtttgt ttattgctca tgttctgcga    8760
cttgcttgca acgatacagg tgtcggctcg ctagacggga gacttttgtt ttgcttttct    8820
aatattctcc tggagaggtt tacgatcatg gctcgattct tatgagtttg gactttacag    8880
tacgttaggc caaccagttt cctcatttac ctatacatag tgtttcaacc tcagatgaat    8940
ttttctcatt ttttcttcta ttctgtcgtt ccaacgtgat ctgctccttc catacgatgg    9000 tattacctttt cgccagtcaa tccaattgcc tgggattttta ctcactcgag tctgcttcgc    9060
atgatgtaca tgaccttccg cctggagaca atttgttgtt catcactcta cgattcgaat    9120
tgcgtgctct cgccgtacca tctcatttca aactttccag ctctgctttt gagactcaat    9180
tctgccagct catgcagcac cgaatacctg ctctggtaag gatcctctga ttcttgctac    9240
ttcacgccat catctgcact ctgaaagtgg tttgagctga tcgtagtata gtctttgttg    9300
atcatcgtgg gcgatcatca gcaaccaaac tattgagatc gatatacgct cgcggtactc    9360
atgtacctct ccgcacaata ggttcaggat cagatccctc atcatctcac agatgtccga    9420
aaatactccc ttgatcaaca acaccaccag gtacagtacg tacatgtact gccctgcata    9480
tcaaactcac agtgtacaag catccaaagc taatgtcatg aacttacacc aatcctctga    9540
gttctccgcg gctgggagat aggatgaagt tcagccacca cagtgacgcc tttcaaggtt    9600
gaatgacaga ttccaaggtt ggttgctctt atcgacggcc cagagcttca agtatacttg    9660
tcactgaacg aaggtgtggc tgatccggag aaccaaagac aactggcata actccaacct    9720
tcgtgaacat gtgaagagta cttgagctag agcaaaagcc agagcgctag ggacgggcac    9780
```

```
tgacccgcca cgtacggaga acccctccac aagaagattc cggaggaagg tccaccagag   9840
cccacaaaga gagttagcag aggcaataac cgacgattag cttatttgca ccaggatcca   9900
cctcattctg tttacggccg gattagagga taccaccagc catgtttatg agattgacat   9960
gtgaaaggat acaattgacc ggttccgcgc acgataagaa agaaaagacg cagaaaagag  10020
tgggagagcc gagaaggacc aaccgaagac gtgataaggg catatttcgc tctttagggg  10080
agcaggatga ccccggatgt tgactcagc taagttggca gcctgtcagc actacgaaag   10140
cgacatcctt cgacactccc acggcatcaa caatacaatg cggatctcgt gctttgctcc  10200
ataattggca tattgcttca ctgctgggca tagacattga tgagacgatg atcgtatgcg  10260
cacggagacg ttcatcgttg actgcagggg ctgaggcatg ggaatatggc gggtgaggtg  10320
tgccgaccga catgaacgca tcatcaattt ttggatgagg tcttgatgta agcaggtgtg  10380
gttgatggct ggaagggtct gtgctt                                       10406

<210> SEQ ID NO 4
<211> LENGTH: 5611
<212> TYPE: DNA
<213> ORGANISM: Aureobasidium pullulans

<400> SEQUENCE: 4
tcttgaagca gtgtattggc gtcagaggag acatactgac tctcattcca ggtcacatcg     60
actggcacat gcaacaaggt ctggctgcta ctttcatcga ggcacctctc gagatgcaga    120
aaaccctcag tgtgccagat gaccactatg ccgcctgtaa agccgctggc gttcccttcg    180
caggaaatgc agccgcaaac acaaagatg tactagacct gagcggccag aacaagccgg     240
cccgcccggt tcctgcaggc tttacggcca ggggcattgt ggcactggtt ttcagctgta    300
tcgcagcatt tgtaggtttg gcagcaatca cctggtaagt catccgaaga tcacgttcca    360
caagatcgcg atgtgtgtag cagtggctga cgcaagaatg atacaggtac ggaatggcac    420
cgctaaatgc gagtgagcaa gaaagagtag tagcttcaac agtcagcaca gccgacgagt    480
agtggatgtg gaaagatgca tcgtcacact tggtgagatg tgcaatcaag gacgagtcaa    540
tggtgtacca tgaaatcttc tcaagttctc aagtaatgcg cataaaagca aaaatgcaag    600
gagtacttgc aagaatccat tgacgttggc caatcgagga agctgtctgc ttgatgctct    660
gtttgatcga gggagctcgc atgttcccag actcttatta gcttccagaa gacccttgtc    720
gaccgagttc tccgagacac aagggagctg ctcgcaacgg tgtaatcctt gtacaagact    780
atcgttgaga actaagagaa gctgcaatct ttcatttagg ttttgatgtc ggaccttgct    840
gagccatcac tggagacctt cggcatgccg aggcatgccg aaaaggcctt cttcttgatg    900
gttttcacgc cgcgtgcttc cgtagaacac ttatacagag gtggtgttgc tccttgttcc    960
gttcccagga gatcgcgggc ttgggggcaa gtgcggaatg agccaagatc aagtcttccg   1020
tagtctttgg aagatgcaag tcactggcat atgtacatac ccagactcga cgtgggtag    1080 gcgttatctg tatacgttat acggtggttg gtcaaaaggt cagtcgttga caagctgacc   1140
caaaagaacg cgactattgc tgcagatctg cagctattca atgtttgaac ataacgagcc   1200
cagagtgatg gtgtgtagcg catgcacaat ggtcagcgga aggatgtgtt gtcaatcttg   1260
tgtcactgag atgaatcttg attccctcag tgcgaccgtc atagtaaaca actagatgct   1320
cgtaatatgt cggcctttca agacatcaac aagatgcgga aagacagggg caggcagaaa   1380
accgtggggt gagggaaaga gaaggacaag ttcaacgaca gggtttggca ggaattggcg   1440
agcaaattga tgtacgtctt gcagatcaga ggcagctgtg gtccaccgtt gtgggccttt   1500
```

```
ccaggccgca ttacatggct tggcttgagc tgcgagcatg ccgcaacttg caagactttc    1560
agacaagcgt caagcagtgc aaatttgagc caagagaggc ggtgacaagc gtgcaggggc    1620
agcaggagtt gacagaatct gtcaacaaac agcctcgtcc ctgcattggc gtgtgactgt    1680
ggtcaagcag aatcttgtgc tttggtggac ggcggcaggt tcgagacag catccgaaaa    1740 ccctcgggtc gcaccccact tcagaggct tttgagctgg cagctgttgg gttggtggca    1800
ggacgagtcg gctcctgcgc gcacgcagct tgtcaaaaag aagcataaag acgtgtgtac    1860
agtatggcca tctctcactc cttcttctgc ccgactatca gaaacttcct cagcgtgcct    1920
gtctctcggg tcgtgccttc gtatttgact tgtgtctgtg tacctacttc acactggtgg    1980
ccgtgtgctc tcgctttgac ttgctcggcg caaatctcga ctggtctcag cggtctgggc    2040
tggtgcccct cggtcgtcac ttaatatttt gcttcccttg caacttccag tctggtactc    2100
tgtgtgcacg catcctttca ccttggttac cccatagcac ttgacaactg tctgaccacc    2160
ccatcttgga catctccacc ctgcctcact ccgcttcaat ccaccgagcc tctctgtcaa    2220
tttaggcgct caaaatgtct cgtcacgcaa ccatcaccca gtcataccaa gagcgcgctt    2280
cgctgcccaa gacatcgccc gtggcctctt atcttttgcg attgattgcc gcaaagcaga    2340
cgaacctctg tgtttcggcc gatgtatcca ccacaagaga gctcttgcag ctcgccgaag    2400
aagtcggcga ctcaatatgc atgctcaaga cacacgcaga cattatcaat gactttggcc    2460
ctcgcaccat ccaaggtctg aaagagattg ccgccaaaaa gcacttcctc gttttcgaag    2520
atcgcaagtt tggcgacatc ggtagtacgt caatgctccg gtgctgtatg acttttatca    2580
gccactgaca gctgctcgca ggcacggtgc agaagcagtt caccgctggt cccctacaaa    2640
tcgtacgctg ggccaacatc atcaatgctc acatctttcc tggccccgcc atcataaccg    2700
ctctctcgca agccgcccac gatgctgtta cctcgctcaa taccgccgtg accacttcca    2760
tctcagcctc acccgtccct tcgtatatgg atgacagtga cgaagccgag tcccctgcct    2820
tgtctcacca tgacgattca gatgatcttg acaggctctc cagcgacgaa gacaccaacc    2880
agctgtctac atacaatgac cctactggtc gcaagcctag tgtcgtttca gtctctacca    2940
ccatcagcac aaagacagaa agcatctcac ctcaacccac accaacccac ctcggtggtc    3000
cttccgactc catctcggct atcagtgcag gctcgaccag tcaagaatcc tcagctttgg    3060
ctcgcctcgg cgaaccccct ctccttcgaa gcttgctcat tctcgcagag atgagcagcg    3120
cgggtaattt gatgactggt gcatacacgg agcaatgtgt ggttgaagca cgcaaaaacc    3180
cggagttcgt catgggcttc attgcacaac gctccttgaa cgagaagcct ggtgacaact    3240
tcatcaccat gacccctggc gtgcaaatcg gagctactgg agacggtctc ggccagcaat    3300
acaacacccc agagaaggtt atctgcgagg ctggtaccga cattatcatc gttggtcgcg    3360
gtgtttatgg tgcacaagac aagagggcaa aggccgagga atacagaatc agaggttgga    3420
aggcatacga ggagagaatc ggctcttctg caacaaagc cacaaggtga acaatatacc    3480
aacatatatc aagatgagga cattcacctc tgcgaaagag gaagagcaga ttcttttgg    3540 tcgggcacca acaggaaaca aaagaaatta ctgggacttg gtagaacaga ctggaaactt    3600
cagatcggat ctcatgtttg gagaacttct acatatcgcg atgcaggtat acaaaaaagt    3660
gtagagcggc tctctgaagc cgtccgttat ttccttctgt ttggtctcag gccttactat    3720
ccggaacaat tcacctttgg tgctgagtcg gttcgcgcgg cacgaaattt gattgatcag    3780
cacatggccc cctatgatgc cgtatacaat ggctccactg catgccaatc aaccggcaaa    3840
```

```
acatggtcca actttcggca ggcgaaattg gatctttgat gtttgccctt tgagcgtttg    3900
ctgagtgata taacagatgg ttacactcga tgtcaaaagg tctttggata atgtcgttgt    3960
gataccacag ctcgcctatg aaccattgtc aattttttgta taccatcttt tacagtgatt   4020
actgcttatc tatgtgaaag tccagctcac tcgagtatgc aagagattga ccgaaggaat    4080
agcgaacgtt cgggccgacc ttgataccag aaaaatagggg ctgtgacatg aggagtttga   4140
tatacataca cacagcgatg aaagtggtgc tgatacgcat gtcaagatat atataagacg    4200
ggtggatgtt ttatcacgtc cacaaccttt cattggccat gaaaagatct ctagtatcga    4260
gatgcttgaa caaatggctt tgagcctgcc gattcttgta gtgctgatgc atgcttgcgc    4320
cagcagaatc tttcttccac atgagcgggc gcttgactt agaccaggcg tagtcatgtc     4380
tgcagtcttg ccaacaccac cagcatacgc ctacttcgcc tagagcaagc accagaagat    4440
ctagtagagg catgatgcgt gtgcggatac cacagtggtg atgattcttg tctacctgat    4500
actcaggggc ttgcttgaaa ctgtcgacta gatccaggat gtcgccttca tatggttccg    4560
gagattccgt ggttgcaaag atggtacctt ccaacgagag ggtgttgata cgtttgaaga    4620
atttgactgt ttgtcccagc tggaacatgt cgcattcagc gcttgaatcg taaccgagct    4680
tacattgcct ctcgcgagac gtgtataatg tgaggaaatg tgtctgtatc gactgagcgg    4740
tctggagtat gcagtcccgc cggaaaagca actcgtcttc cattcccacg ggaagatccc    4800
accacagagc agcatcttct tcaggctcac gaccgaccca gcctcggtgt atgagacgca    4860
gagatgcttg atatacccag cttgcattgt ccaagaaaat tccaactagt aaacgttgtc    4920
gcgtgcgctc ttctgtccat gtggaagcaa ctttttgtatt cgacttgccg tccagagcgg   4980
caattatctt gtgactcttg cagtaggcac gccatggctc gaggcagtcg aagcggtcgg    5040
ctacgatgca gaggttggcg atatttgcca gaggtggagt aagggtggtc aagtcgcgag    5100
cgtgcaaggc gcacagaaag tcggccatga gcggtttgat tgtcttgacc ataggcgata    5160
tgcggccgac gtccacaatc ttgatttcgg ggagctcatc ggcaggtacg gatgcgtcca    5220
aggttgtgta tttggtcctg aggtctgcgt gggcaagagc gacggtagtg ccttcctggt    5280
agtcgcctga aagagtcga ctaaagtagc tcgaggcttc tttcaacccg gccgagtcga    5340 cacggtatt gcatgtctct tgtgtgggag tgtctcgttg aaccagcagt acgacgtctc    5400
ctgctggcga gatgatggtg attccggacg gggtttcttc caagttgttg gcagtcttgt    5460
tctcttgcgg gtcgcgtttg gcagcttttg gtttctttgt tggagttgac atggccggga    5520
gccgttcaga gacactgtct ttatggataa ggccagaaca ttgcttcaga ggtggcgtgc    5580
gaagaatgtt tttgccaatc aagtacctat c                                   5611
```

<210> SEQ ID NO 5
<211> LENGTH: 6036
<212> TYPE: DNA
<213> ORGANISM: Artificial Sequence
<220> FEATURE:
<223> OTHER INFORMATION: Chemically Synthesized

<400> SEQUENCE: 5

```
gacccgccgc tctttgacct acagtttcgg aagtatcagt cttggaagct tggtagttgc      60
aatcatcaac atgctcagac aagcatgcag tattgcacgt cagcaagaag caaattctgg    120
aaacatcgct gccgacattg cgcttttgcat tcttcagtgt ctcattggaa tcttggactg    180
ggctgtccag ttcatcaacg taagtgggaa tcttacccga gacgcgatat ttcgaaattt    240
ccagacagct cacgaaagga tagagatacg ctttcagcta catcgcgctt tacggcaaag    300
```

```
cctatattcc cgccgccaag gacacttgga cgtatgtacc tcatctatac gaacaatgag    360
gccccactga caacaacaat tagtttaatc aaagacagag gtatcgatgc gttagtcaac    420
gaatgcctga ttggccccgt cttgacccag ggcgctacgg ccatcgctta cctgtgcgct    480
cttttggcct acctgtacct gatcttcacc tcgcctgcgt acaacagcaa cggcgagtac    540
acacccgtgg ttgtcgcatt cgcgttcttg attggtctgc aaattgccaa catcttcaca    600
accccgctaa gcagtggtat cgacactata ttcgttgctg cagctttcga cccgcaagta    660
atgatcacag aacacccgga cctgtacgcc aagctggtgt cgacatatcc gcatgttcag    720
caggccattc atgcttaaag cagatgatcg caatcattcg ctagttctag cagtttcggc    780
cgcgggatat tttttgtttg aactacagat tacaaggcc atatccgtttt attcttgttg    840 ggcaaaaccg ggcgctcccc tgtcgattcg cgtatcgttg cgtcagataa gggttcaggt    900
gtcagggcct ctcgggtcta cggataatcg cgaatcgaag gatacccaaa ccacaggact    960
cttgatacca cagcttaatc gccctttttt tctttgcagt agtcaagtaa tacgtaataa   1020
cagaacacca cgctcgtttc gcatgactcc attaccagat gtcgtagtac atgttacagc   1080
aagatattgt agagagatac gagatcttac cgcaacacac atgccgtggt cactcacgat   1140
cggcacagca agcccatagc gtgacaagcg ctcgatctgg ttagcacatg attttccgcg   1200
agcggccgct ggcaaggccc gaggacccta acggcgatgg cgactcgatg ctacgaagt    1260 tggcaacaac aaaaagtgac aagcaaacgc ctttggggcc gtgcttgcca gcctcaaaag   1320
ccccaaagcc tcaaacgtca gcccggccaa gagggagga gtgacgtgcg ggcagctaaa    1380
cgtcgtcata tgggtggtgc ggggagagta ggttgggatg gtgcgggttg gcgcttgatc   1440
agtgtgatgt tagggagcaa cgaggcatta acctgttgct tcccccccag tgtggttaaa   1500
tagacttggt atccctcgac ctcttgtttt gtcattctca tctcatactt ccttcaccca   1560
atccgaaaga acctctttct cgtttcccct ctagtactat tcttcgttca gagccaacca   1620
ttggttaggt tcgtgctatc tgcccctcgt tccgcgataa ccccaccaca ttgctgacct   1680
cttatctaca ggacaaaagt acatcaacac cgaccactat accagactat atacaaaggt   1740
tagtacccaa tgactgtctc tgatgcgctc gagggtcatt gtcatcatca ttctgaacgg   1800
tgtgatggct ttgttcccct cccggctagg cgcgcgatta ttcacagcgg caaatcgtga   1860
gcaacgggag gacccaagtg tgcagatgca gatgtgacaa gtgtgaggct ggacgagcgg   1920
tgtgccggaa aaattggagg aatgggaggg aaagcggcgg ctctgtagcc ctcgctgatg   1980
tccgacttct tccctccaa acgttatcga tagcgaaaat actacgtagt gagcggagcg    2040
cctctacaag gcggaacaga attggcttca ccgcgaatag ggcgagtgag agcagttaat   2100
cacgtggagt ggatagttgt ggccctgttg agacaccgca gtaaaagata cacacatcaa   2160
ttcacgattg ctgcagttcg cctccgccac cacggtccat agcaagaaaa aaacgacaga   2220
aacgacagat ccgttacatc acttgtcctt caggctccgc ttgggctccc aacgaagctg   2280
caaaaaagtg aaagaaaaaa aactagcttg gcggggcaac tgaagctaga ccctattctc   2340
gcttagtcag tgcgcgctct cacacaacac tcaaaaaggc caccctcc gcaccctctt     2400 ctcaacaccg tcttcatacc acggttcatc aagcaatcgt atctggtaag ctttgacccct  2460 cgagctggct ccactttgct atttcttgga tctgctcgtc ttttcttcc ttcctcttct    2520 ttttctaacc tctcttcaga aagttcaact gtacttcact caatcttcca tacacaaccg   2580
tcaagatatc ctgccgatat gaaaaagcct gaactcaccg cgacgtctgt cgagaagttt   2640
```

```
ctgatcgaaa agttcgacag cgtctccgac ctgatgcagc tctcggaggg cgaagaatct   2700
cgtgctttca gcttcgatgt aggagggcgt ggatatgtcc tgcgggtaaa tagctgcgcc   2760
gatggtttct acaaagatcg ttatgtttat cggcactttg catcggccgc gctcccgatt   2820
ccggaagtgc ttgacattgg ggaattcagc gagagcctga cctattgcat ctcccgccgt   2880
gcacagggtg tcacgttgca agacctgcct gaaaccgaac tgcccgctgt tctgcagccg   2940
gtcgcggagg ccatggatgc gatcgctgcg gccgatctta ccagacgag cgggttcggc   3000 ccattcggac cgcaaggaat cggtcaatac actacatggc gtgatttcat atgcgcgatt   3060
gctgatcccc atgtgtatca ctggcaaact gtgatggacg acaccgtcag tgcgtccgtc   3120
gcgcaggctc tcgatgagct gatgctttgg gccgaggact gccccgaagt ccggcacctc   3180
gtgcacgcgg atttcggctc caacaatgtc ctgacggaca atggccgcat aacagcggtc   3240
attgactgga gcgaggcgat gttcggggat tcccaatacg aggtcgccaa catcttcttc   3300
tggaggccgt ggttggcttg tatggagcag cagacgcgct acttcgagcg gaggcatccg   3360
gagcttgcag gatcgccgcg gctccgggcg tatatgctcc gcattggtct tgaccaactc   3420
tatcagagct tggttgacgg caatttcgat gatgcagctt gggcgcaggg tcgatgcgac   3480
gcaatcgtcc gatccggagc cgggactgtc gggcgtacac aaatcgcccg cagaagcgcg   3540
gccgtctgga ccgatggctg tgtagaagta ctcgccgata gtggaaaccg acgccccagc   3600
actcgtccga gggcaaagga atagagtaga tgccgaccgg gatccactta acgttactga   3660
aatcatcaaa cagcttgacg aatctggata taagatcgtt ggtgtcgatg tcagctccgg   3720
agttgagaca aatggtgttc aggatctcga taagatacgt tcatttgtcc aagcagcaaa   3780
gagtgccttc tagtgattta atagctccat gtcaacaaga ataaaacgcg tttcgggttt   3840
acctcttcca gatacagctc atctgcaatg cattaatgca ttggacctcg caaccctagt   3900
acgcccttca ggctccggcg aagcagaaga atagcttagc agagtctatt ttcattttcg   3960
ggagacgaga tcaagcagat caacggtcgt caagagacct acgagactga ggaatccgct   4020
cttggctcca cgcgactata tatttgtctc taattgtact ttgacatgct cctcttcttt   4080
actctgatag cttgactatg aaaattccgt caccagcccc tgggttcgca agataattg    4140 cactgttttct tccttgaact ctcaagccta caggacacac attcatcgta ggtataaacc   4200
tcgaaaatca ttcctactaa gatgggtata caatagtaac catggttgcc tagtgaatgc   4260
tccgtaacac ccaatacgcc ggccggcgtg tcggtcgtgc tcctctccgc aagctttcgc   4320
gcaacgagcg tttcattggt cctgctgctc atcttgcaga gatgggagcc aagtacgatg   4380
ctcttcttgg tggcattgag atgtgtcttc gcttccagaa cgtcgagggt gatgacgagt   4440
cattcgagct tgccaagatc ctcaaggaga actcttcgag cgatgctact gagaagatca   4500
ccggccttga gcgtgaacac aaactcttct cagcagttga ggaagttgtc aagaaggtcc   4560
aagcttgact acctcagcag cgcgccaccc gtaatcgcag gcgactggaa cgtctttgat   4620
tgttggtagc cagacatggg gtgatgcgac gaaaccacga gatacgcagc attgaaattt   4680
ggcattggtg ttcaggattt gggatttgga aggattagca ctgggttagc atgttacccg   4740
atattaggca acgggcgtta gtagcaggta gcatggattc accaaattga caaagctcct   4800
gggaacagtt gagcatacgt tttatcaaga tgatagaccc tctcacgtat agccttttgg   4860
aagcgtccga acctgaggaa caagcctggc tttctcagat aacaagccag aactttcatg   4920
cgtttctgct aaatggttgc aaattcaaat gtgagttgtg cgtgactgaa atgtaattcg   4980
aggtggctct ttgagcaatg cagtagttga tggtcggtca tgcgaaagtg aaacaggtga   5040
```

```
aagaaaggtg ctggtgttat caaagacaag ccagcgtgcg tcatttcccc cgcaagcgca   5100
accgcagtga gagtcgcctt tccattgtca tcaccagggc ccaatcaatc aatttgtgtg   5160
gtgtctgctc tgcctttgat ccctaaacat ccgacactct cctcgaagcc catctagcaa   5220
cagcatggcc atcgacagca taccgtgagt gccttgccac caggcccttg ttgaacaatt   5280
atcctgctca agactattca gtgctaatta gaatgtagat accctgatac cgatcgcctg   5340
gcatatcccg acaagacctt ctacccagtc aagatcccca tctcgtgagt ctaaggagac   5400
agaattatgc acactggact gatatcgatg cgctagccac tggcaattac gacactacat   5460
ctcgtcgccc gacaaggacg ccatctacta cgccagcgtc aacgaagttt actatctcga   5520
cacgcactcg cgcaaacgta ataccttgc cacactacca ttcgtcgccc gatgtactgc   5580
ctctggtttt ggctgggtct gtgtcggagg tgaggaggag ggttacttcg ccgcaataaa   5640
gctagaaggc tcgtctccgg ttcgccctgc agatgtagat gctccactgc cactggacta   5700
ctggcaatcc cagagaggca ccccaagagc cgccaacgtc aagcttgaac acataggcga   5760
agagattgtc aactccattt ccatccacca aatccatgat gaagacaacc acctttacga   5820
tgtcgtcgcc gtcctgacca acaatgacaa gactgttcgc gtctactcgc ttactcaagc   5880
tttgaaaact gcagtgttgg acctgccctt ccccatgaat cacgcctcca tatctcctga   5940
tggtaccact cttgttgctg tcggcgattc taaccaagcc ttttctata cacgcacact   6000 atcgcagcct cctccacaga ttccaaagcc ccacaa                             6036

<210> SEQ ID NO 6
<211> LENGTH: 5514
<212> TYPE: DNA
<213> ORGANISM: Artificial Sequence
<220> FEATURE:
<223> OTHER INFORMATION: Chemically Synthesized

<400> SEQUENCE: 6
ggctttgggc gcataccgag agcattctca atgtccaaga tggtagagtt ggtagagagg     60
aaggtcgagg gaagatcaat accggtcttc tcgcgaagtt cactgagaat agtcaagctc    120
atcaacgagt ccataccaag ctcggaaagg tctgcttcat cagtaagctc ggagctgtca    180
attcccatct cctggacgat gatgtggcga gccaagctga cttcaccaac ttcggagtca    240
ggaatctcgc gggtaggaga gtcaatatca ggctttccag catcgctggg tgcagtgcta    300
ggcgcagagc tggcggggt gctcaggtca tcctcgtaag gagtggcaat gtctgagggc    360
tcagactcgt cctcggaatc atcttcaacc ggaccaacgt taccatcgaa ctgagagaag    420
tacttcttca tctcgccaac agtagggtaa tcggtgaaaa gggtggagct gatctccatg    480
tcaaggtcct ctctgaactt ggcagagatg gtcagcgaca tgagagagtc aacaccaagg    540
ttctcgaatg cagcctcgtc aacaagctca gactgctcaa catcggtctc ggtagcaatg    600
atttgcatga cacgagaagt aatggtagcg ccttgagact tctttgcagc gaccttcttg    660
ggagccttag cagccttgac agcaggcttg ggggcctgag cctaggagc ggcagccttg     720 ggggcagcaa ctgcctttgg agcggcagcg ggagcggcag gggcagcagc cttggcaggt    780
gcgccagcct tctgaggagg caggaagacg ttcaggacag ggcgagggat ctgttggaac    840
ttgagaccac cgcaaacggc gacaatctcg tctccctcca tgatgtaaac atcaccttgg    900
tagatgttac caggcttggg aagcatgcga acgtaagagc ggtagttgcc ctcaggagtc    960
aactgcttgg cgattctcat cgaaccccag ccgtgcgaga tgcagacgtt gttgtcggag   1020
```

```
tcaatcagat cggtggcgtt gacaatgaaa cctgagatgt ggcacatgct gtcaatctgg    1080
taagggGCCt ggtaccagtc accatcggcg ggaccgttct ggaacttaac agaagctgta    1140
gcttcagtgg tctggctgtt aacaatgacc tcttccatac cgcggtactt ctcgttgtag    1200
ttgacgaagc acttgaagag cttgtaggcc ataccacgct gcatgacgtg agcctcctgc    1260
gtcttggtct tagccttaag aacatcgacc tgagacttga ccatgaagtt gatacgctcc    1320
caatcctcgt tccaggagct gatgtcctcg aacttgacca gacagtgagc atggtcttga    1380
atgagcttgc cttccggagt aacgcttctg aacttcaggt gagcgacacc ctcgtcaagg    1440
tcagccttgg cctcgagttg gatgtgctgg ccttcagccg gctaggcgcg cgattattca    1500
cagcggcaaa tcgtgagcaa cgggaggacc caagtgtgca gatgcagatg tgacaagtgt    1560
gaggctggac gagcggtgtg ccggaaaaat tggaggaatg ggagggaaag cggcggctct    1620
gtagccctcg ctgatgtccg acttcttccc ctccaaacgt tatcgatagc gaaaatacta    1680
cgtagtgagc ggagcgcctc tacaaggcgg aacagaattg gcttcaccgc gaatagggcg    1740
agtgagagca gttaatcacg tggagtggat agttgtggcc ctgttgagac accgcagtaa    1800
aagatacaca catcaattca cgattgctgc agttcgcctc cgccaccacg gtccatagca    1860
agaaaaaaac gacagaaacg acagatccgt tacatcactt gtccttcagg ctccgcttgg    1920
gctcccaacg aagctgcaaa aaagtgaaag aaaaaaaact agcttggcgg ggcaactgaa    1980
gctagaccct attctcgctt agtcagtgcg cgctctcaca caacactcaa aaaggccacc    2040
cctcccgcac cctcttctca acaccgtctt cataccacgg ttcatcaagc aatcgtatct    2100
ggtaagcttt gaccctcgag ctggctccac tttgctattt cttggatctg ctcgtcctTt    2160
tcttccttcc tcttcttttt ctaacctctc ttcagaaagt tcaactgtac ttcactcaat    2220
cttccataca caaccgtcaa gatatcctgc cgatatgaaa aagcctgaac tcaccgcgac    2280
gtctgtcgag aagtttctga tcgaaaagtt cgacagcgtc tccgacctga tgcagctctc    2340
ggagggcgaa gaatctcgtg ctttcagctt cgatgtagga gggcgtggat atgtcctgcg    2400
ggtaaatagc tgcgccgatg gtttctacaa agatcgttat gtttatcggc actttgcatc    2460
ggccgcgctc ccgattccgg aagtgcttga cattggggaa ttcagcgaga gcctgaccta    2520
ttgcatctcc cgccgtgcac agggtgtcac gttgcaagac ctgcctgaaa ccgaactgcc    2580
cgctgttctg cagccggtcg cggaggccat ggatgcgatc gctgcggccg atcttagcca    2640
gacgagcggg ttcggcccat tcggaccgca aggaatcggt caatacacta catggcgtga    2700
tttcatatgc gcgattgctg atccccatgt gtatcactgg caaactgtga tggacgacac    2760
cgtcagtgcg tccgtcgcgc aggctctcga tgagctgatg ctttgggccg aggactgccc    2820
cgaagtccgg cacctcgtgc acgcggattt cggctccaac aatgtcctga cggacaatgg    2880
ccgcataaca gcggtcattg actggagcga ggcgatgttc ggggattccc aatacgaggt    2940
cgccaacatc ttcttctgga ggccgtggtt ggcttgtatg gagcagcaga cgcgctactt    3000
cgagcggagg catccggagc ttgcaggatc gccgcggctc cgggcgtata tgctccgcat    3060
tggtcttgac caactctatc agagcttggt tgacggcaat ttcgatgatg cagcttgggc    3120
gcagggtcga tgcgacgcaa tcgtccgatc cggagccggg actgtcgggc gtacacaaat    3180
cgcccgcaga agcgcggccg tctggaccga tggctgtgta gaagtactcg ccgatagtgg    3240
aaaccgacgc cccagcactc gtccgagggc aaaggaatag agtagatgcc gaccgggatc    3300
cacttaacgt tactgaaatc atcaaacagc ttgacgaatc tggatataag atcgttggtg    3360
tcgatgtcag ctccggagtt gagacaaatg gtgttcagga tctcgataag atacgttcat    3420
```

```
ttgtccaagc agcaaagagt gccttctagt gatttaatag ctccatgtca acaagaataa    3480
aacgcgtttc gggtttacct cttccagata cagctcatct gcaatgcatt aatgcattgg    3540
acctcgcaac cctagtacgc ccttcaggct ccggcgaagc agaagaatag cttagcagag    3600
tctattttca ttttcgggag acgagatcaa gcagatcaac ggtcgtcaag agacctacga    3660
gactgaggaa tccgctcttg gctccacgcg actatatatt tgtctctaat tgtactttga    3720
catgctcctc ttctttactc tgatagcttg actatgaaaa ttccgtcacc agccctgggg    3780
ttcgcaaaga taattgcact gtttcttcct tgaactctca agcctacagg acacacattc    3840
atcgtaggta taaacctcga aaatcattcc tactaagatg ggtatacaat agtaaccatg    3900
gttgcctagt gaatgctccg taacacccaa tacgccggcc ggtcggccag cgcatcctcg    3960
tatctcttga ggacaacggt accacaacca tcaccacggc agtaaccatc agcagcgttg    4020
tcgtaagtct tgcaagaacc tgtctttgac aggaattggc ccttggaaag accagagaaa    4080
atgtcagggt tggtgaggac gttcagacca ccagcacaag cggtgtcgca gtcaccggcc    4140
cacagcgaag tgcaggcaag ctggatagca gccaagacg acgaacaagc agtatcgatt    4200
gaaaacgaag gaccactgaa cttgaagtag tagttgatgc gaccaggtgc aaaagcacgc    4260
acaccaccag tgatgaagta ggtatcaacg ttctcggaag cgttgatctc acgccaatca    4320
tcagaggttt gaccgtagaa ggtaccaatg cggtggagct tagtagaggg ggtacggtta    4380
gggacgtaac ctgattgctc aagagcctcg taagcagtga caagggccag acgacccata    4440
ggatcagtct gggcagcttc acgaggagac atgttgaaga agcgaggatc aaaaagacca    4500
ggctcgtcaa tgaagcaacc gtaaggagtg tgcgacttgt tcttgcccttt tccagaggga    4560
tcacagtgag cgtctgcatc gaaacggtcg gagggaatct tgcgatgaac atcgagaccc    4620
ttctcgagaa gttcccagag agcctcggta ctggcagcgc tggggaaacg accagacata    4680
ccaacgatgg caatcttgtc gttctgggtg cgaccgtggg tagcatcagt gacggcagac    4740
tcccaggcag agtggtcaac gagggagacc gaggattgac cgccagcttt gatggccgag    4800
acgaggctgt tagatacgtt gctgacacca atgcagaaga ccttggcaga agcattggtg    4860
ttggcggtga tctgagaaac gctctcctca aggaggttgt tccagccaac aggagatctg    4920
agcatgtcgt tcagggacaa cttgaaaagc tcgaaggtgt tctcggcaat gtggcacatg    4980
ccagtcgagc cggagtggac caacgaacga ggctgataag cctggaggag cttggcagac    5040
tcctcgccaa tgatggcgtc aatatcggca ctgctgtaga ggtgctcggc atggtaagga    5100
gcgtagacag gaatcttgac gcggttgttc ttgcgaacag cctcggactc ctcaaagaag    5160
cgcttagtgg tggtgggagg accgctgata gtgatggcca ttgtgctgac agcgctaatg    5220
taagcgtggc tggtggtggg aatgccagca gactcgtgga aagcgttcag agcctccttg    5280
gcagactgct cgttgatgcc agtaacgata gtagaccagc tctccctgga catgaggtcc    5340
tgacccaaag cggttctggc ttcgttgacg cgaacaccag tgcggaaggc gatgcgaaca    5400
gtctctacac caagagtgac gagctcatcg agagtcctgg cggaagcgac ggcggcagcg    5460
gcaagcgatc ctgtgcagag agcaaggatg cgagtgttgg cagcaggagg aagc         5514
```

<210> SEQ ID NO 7
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 7
ggctagrygc rcgaytatyc ac                                    22

<210> SEQ ID NO 8
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 8
gttgacggtk rtgtatggaa g                                     21

<210> SEQ ID NO 9
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 9
gcaggtcgac ggctaggcgc gcgattattc                            30

<210> SEQ ID NO 10
<211> LENGTH: 36
<212> TYPE: DNA
<213> ORGANISM: Artificial Sequence
<220> FEATURE:
<223> OTHER INFORMATION: Chemically Synthesized

<400> SEQUENCE: 10
gcaggatatc ttgacggttg tgtatggaag attgag                     36

<210> SEQ ID NO 11
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 11
cggctaggcg cgcgattatt c                                     21

<210> SEQ ID NO 12
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 12
cggccggcgt attgggtgtt a                                     21

<210> SEQ ID NO 13
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 13
cgtaatcatg gtcatagctg tttcc                                 25

<210> SEQ ID NO 14
<211> LENGTH: 21

```
<212> TYPE: DNA
<213> ORGANISM: Artificial Sequence
<220> FEATURE:
<223> OTHER INFORMATION: Chemically Synthesized

<400> SEQUENCE: 14
gcactggccg tcgttttaca a                                          21

<210> SEQ ID NO 15
<211> LENGTH: 54
<212> TYPE: DNA
<213> ORGANISM: Artificial Sequence
<220> FEATURE:
<223> OTHER INFORMATION: Chemically Synthesized

<400> SEQUENCE: 15
gtcacgacgt tgtaaaacga cggccagtgc gacccgccgc tctttgacct acag      54

<210> SEQ ID NO 16
<211> LENGTH: 50
<212> TYPE: DNA
<213> ORGANISM: Artificial Sequence
<220> FEATURE:
<223> OTHER INFORMATION: Chemically Synthesized

<400> SEQUENCE: 16
gctgtgaata atcgcgcgcc tagccgggag gggaacaaag ccatcacacc           50

<210> SEQ ID NO 17
<211> LENGTH: 49
<212> TYPE: DNA
<213> ORGANISM: Artificial Sequence
<220> FEATURE:
<223> OTHER INFORMATION: Chemically Synthesized

<400> SEQUENCE: 17
gctccgtaac acccaatacg ccggccggcg tgtcggtcgt gctcctctc            49

<210> SEQ ID NO 18
<211> LENGTH: 55
<212> TYPE: DNA
<213> ORGANISM: Artificial Sequence
<220> FEATURE:
<223> OTHER INFORMATION: Chemically Synthesized

<400> SEQUENCE: 18
cacacaggaa acagctatga ccatgattac gttgtggggc tttggaatct gtgga     55

<210> SEQ ID NO 19
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 19
gcggcaacat cggtcgtgg                                             19

<210> SEQ ID NO 20
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 20
```
cattccttgc cgcggttgta g                                                   21

<210> SEQ ID NO 21
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 21
tcaagcgcca aggttatcgg tctg                                                24

<210> SEQ ID NO 22
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 22
gccgctttcc ctcccattcc                                                     20

<210> SEQ ID NO 23
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 23
gtggcgacga tggaggcttc t                                                   21

<210> SEQ ID NO 24
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 24
agcccctggg ttcgcaaaga taat                                                24

<210> SEQ ID NO 25
<211> LENGTH: 52
<212> TYPE: DNA
<213> ORGANISM: Artificial Sequence
<220> FEATURE:
<223> OTHER INFORMATION: Chemically Synthesized

<400> SEQUENCE: 25
gtcacgacgt tgtaaaacga cggccagtgc ggctttgggc gcataccgag ag                 52

<210> SEQ ID NO 26
<211> LENGTH: 49
<212> TYPE: DNA
<213> ORGANISM: Artificial Sequence
<220> FEATURE:
<223> OTHER INFORMATION: Chemically Synthesized

<400> SEQUENCE: 26
gctgtgaata atcgcgcgcc tagccggctg aaggccagca catccaact                     49

<210> SEQ ID NO 27
<211> LENGTH: 49
<212> TYPE: DNA
<213> ORGANISM: Artificial Sequence

```
<220> FEATURE:
<223> OTHER INFORMATION: Chemically Synthesized

<400> SEQUENCE: 27
gctccgtaac acccaatacg ccggccggtc ggccagcgca tcctcgtat           49

<210> SEQ ID NO 28
<211> LENGTH: 54
<212> TYPE: DNA
<213> ORGANISM: Artificial Sequence
<220> FEATURE:
<223> OTHER INFORMATION: Chemically Synthesized

<400> SEQUENCE: 28
cacacaggaa acagctatga ccatgattac ggcttcctcc tgctgccaac actc      54

<210> SEQ ID NO 29
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 29
tcagggccga tgttagggat gct                                        23

<210> SEQ ID NO 30
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 30
tcggcaggat atcttgacgg ttgt                                       24

<210> SEQ ID NO 31
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 31
gtcccgccgg ctgtaaggtg                                            20

<210> SEQ ID NO 32
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 32
agcccctggg ttcgcaaaga taat                                       24

<210> SEQ ID NO 33
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 33
gcgagcgaga gcgacctgga t                                          21
```

<210> SEQ ID NO 34
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 34
acaacttctc cgctgctggt ggtaa                                                25

<210> SEQ ID NO 35
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 35
ggctttgggc gcataccgag ag                                                  22

<210> SEQ ID NO 36
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 36
gcttcctcct gctgccaaca ctc                                                 23

<210> SEQ ID NO 37
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 37
gacccgccgc tctttgacct acag                                                24

<210> SEQ ID NO 38
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 38
ttgtggggct ttggaatctg tgga                                                24

<210> SEQ ID NO 39
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 39
agctgcgccg atggtttcta caa                                                 23

<210> SEQ ID NO 40
<211> LENGTH: 23
<212> TYPE: DNA
<213> ORGANISM: Artificial Sequence
<220> FEATURE:
<223> OTHER INFORMATION: Chemically Synthesized

```
<400> SEQUENCE: 40
ctggggcgtc ggtttccact atc                                          23

<210> SEQ ID NO 41
<211> LENGTH: 49
<212> TYPE: DNA
<213> ORGANISM: Artificial Sequence
<220> FEATURE:
<223> OTHER INFORMATION: Chemically Synthesized

<400> SEQUENCE: 41
gtcacgacgt tgtaaaacga cggccagtgc cgccgcgtgc ttccgtaga               49

<210> SEQ ID NO 42
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 42
ggtgcgttga tggtgctgat cctcttcctg gatacatcgg ccgaaacaca g            51

<210> SEQ ID NO 43
<211> LENGTH: 55
<212> TYPE: DNA
<213> ORGANISM: Artificial Sequence
<220> FEATURE:
<223> OTHER INFORMATION: Chemically Synthesized

<400> SEQUENCE: 43
cacacaggaa acagctatga ccatgattac ggtaggcgta tgctggtggt gttgg        55

<210> SEQ ID NO 44
<211> LENGTH: 52
<212> TYPE: DNA
<213> ORGANISM: Artificial Sequence
<220> FEATURE:
<223> OTHER INFORMATION: Chemicallty Synthesized

<400> SEQUENCE: 44
ggaagaggat cagcaccatc aacgcaccga gcagcgcggg taatttgatg ac           52

<210> SEQ ID NO 45
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 45
cgccgcgtgc ttccgtaga                                               19

<210> SEQ ID NO 46
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 46
gtaggcgtat gctggtggtg ttgg                                         24

<210> SEQ ID NO 47
```

<211> LENGTH: 24
<212> TYPE: DNA
<213> ORGANISM: Artificial Sequence
<220> FEATURE:
<223> OTHER INFORMATION: Chemically Synthesized

<400> SEQUENCE: 47
tggggtgagg gaaagagaag gaca                                            24

<210> SEQ ID NO 48
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 48
cgctcaaagg gcaaacatca aaga                                            24

<210> SEQ ID NO 49
<211> LENGTH: 52
<212> TYPE: DNA
<213> ORGANISM: Artificial Sequence
<220> FEATURE:
<223> OTHER INFORMATION: Chemically Synthesized

<400> SEQUENCE: 49
gtcacgacgt tgtaaaacga cggccagtgc tgcggagcca acacccagat ag             52

<210> SEQ ID NO 50
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 50
gaacttgtcc ttctctttcc ctcaccccag gaagccaccg acaccaatgt g              51

<210> SEQ ID NO 51
<211> LENGTH: 50
<212> TYPE: DNA
<213> ORGANISM: Artificial Sequence
<220> FEATURE:
<223> OTHER INFORMATION: Chemically Synthesized

<400> SEQUENCE: 51
ggatctttga tgtttgccct ttgagcgact tccgccgtct ctgtttcgtc                50

<210> SEQ ID NO 52
<211> LENGTH: 55
<212> TYPE: DNA
<213> ORGANISM: Artificial Sequence
<220> FEATURE:
<223> OTHER INFORMATION: Chemically Synthesized

<400> SEQUENCE: 52
cacacaggaa acagctatga ccatgattac ggaggctgag gacaaggcaa gagat          55

<210> SEQ ID NO 53
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 53
tgcggagcca acacccagat ag                                              22

<210> SEQ ID NO 54
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 54
cacggcggta ttgagcgagg taa                                             23

<210> SEQ ID NO 55
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 55
gaggctgagg acaaggcaag agat                                            24

<210> SEQ ID NO 56
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 56
gccgcaaagc agacgaacct                                                 20

<210> SEQ ID NO 57
<211> LENGTH: 52
<212> TYPE: DNA
<213> ORGANISM: Artificial Sequence
<220> FEATURE:
<223> OTHER INFORMATION: Chemically Synthesized

<400> SEQUENCE: 57
gtcacgacgt tgtaaaacga cggccagtgc gagtgggcgg agttggcgat ag             52

<210> SEQ ID NO 58
<211> LENGTH: 52
<212> TYPE: DNA
<213> ORGANISM: Artificial Sequence
<220> FEATURE:
<223> OTHER INFORMATION: Chemically Synthesized

<400> SEQUENCE: 58
gaacttgtcc ttctctttcc ctcaccccaa gcggcctcaa tacccatacc ac             52

<210> SEQ ID NO 59
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 59
ggatctttga tgtttgccct ttgagcgctc tgacgcctcc acctacacca c              51

<210> SEQ ID NO 60
<211> LENGTH: 52
<212> TYPE: DNA

```
<213> ORGANISM: Artificial Sequence
<220> FEATURE:
<223> OTHER INFORMATION: Chemicallty Synthesized

<400> SEQUENCE: 60
cacacaggaa acagctatga ccatgattac gttcaccctt cgcccaaact gc          52

<210> SEQ ID NO 61
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 61
gagtgggcgg agttggcgat ag                                          22

<210> SEQ ID NO 62
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 62
ttcacccttc gcccaaactg c                                           21
```

METHODS AND STRAINS FOR PRODUCING BIOPRODUCTS IN *AUREOBASIDIUM PULLULANS*

CROSS-REFERENCE

The present application claims priority to U.S. Provisional Patent Application Ser. No. 62/193,875 filed Jul. 17, 2015, the content of which is expressly incorporated herein by reference.

BACKGROUND OF THE INVENTION

Field of Invention

This invention relates to genetically modified strains of *Aureobasidium pullulans* that are capable of producing desirable bioproducts. By altering the biochemistry of the disclosed strains via genetic manipulation, strains have been produced that no longer produce bio-contaminants such as melanin and melanin-related pigments. The presence of such pigments adds significant cost to the production of bioproducts because they must be removed prior to further processing of the desired products. Additionally, some strains described herein are modified to delete the genes encoding for biosynthetic enzymes that produce undesired products. Therefore, modified strains lacking the capacity of forming less-desired bioproducts have been constructed that form target bioproducts preferentially on cheaper substrates. Utilizing these methods and strains, production of desired products can be achieved under more economically feasible conditions, resulting in a benefit to food, pharmaceutical, industrial, biofuel and other important industries.

Background

*Aureobasidium pullulans* is a yeast-like fungus, perhaps best well-known as the source of the exopolysaccharide pullulan, which is commercially-produced for numerous consumer and industrial applications, such as emulsifiers, thickeners, and edible films (Leathers, Polysaccharides from eukaryotes. In: Vandamme, E. J., De Baets, S., and Steinbuchel, A., Editors. Biopolymers. Weinheim, Germany: Wiley-VCH. p. 1-35 (2002); Singh et al., *Carb. Polymers*, 73(4):515-31, (2008)). *A. pullulans* also produces other useful bioproducts, including industrial enzymes (Leathers et al., *Biotech Lett.*, 35(10):1701-6 (2013); Rich et al., *Enz. Microb. Tech.*, 53(1):33-37 (2013); Liu, et al., *Anton Leeuw Int. J. G.*, 94(2):245-55 (2008); Leathers, *J. Indus. Microbiol.* 4(5):341-7 (1989); Kudanga et al., *J. Basic Microbiol.* 47(2): 138-47 (2007)), the biopolyester poly($\beta$-L-malic acid) (Leathers and Manitchotpisit, *Biotech. Lett.*, 35(1): 83-9 (2013), and numerous bioactive compounds (Wang, et al., Bioresource Tech., 100(9):2639-41 (2009); Chi, et al., *Appl. Microbiol. Biotech.*, 82(5):793-804 (2009); Slightom, et al., *Gene*, 431(1-2):67-79 (2009)), including an extracellular dense "oil" that accumulates on the bottom of the fermentation flask (Nagata, et al., in *Biosci. Biotech. Biochem.*, 57(4):638-42 (1993)). A partial structure of this oil suggested that they were 3,5-dihydroxydecanoyl and 5-hydroxy-2-decanoyl esters of arabitol and mannitol (Kurosawa, et al., *Biosci., Biotech. Biochem.*, 58(11):2057-60 (1994)) and that these polyol lipids exert an anti-proliferative effect on cancer cell lines (Isoda and Nakahara, *J. Ferment. Bioeng.*, 84(5):403-406 (1997)).

Different strains of *A. pullulans* demonstrate different phenotypes with regards to bioproducts produced and can be genetically distinguished from each other. (Manitchotpisit, et al., *Mycol. Res.*, 133(10):1107-20 (1997)). It has been noted that about half of all strains of this filamentous fungus produced oils, with certain genetically-related strains showing the highest yields (Id.; Manitchotpisit, et al., *Biotech. Lett.*, 33(6):1151-57 (2011); Manitchotpisit, et al., *World J. Micro. Biotech.*, 30(8):2199-2204 (2014)). Oil colors range from bright yellow to malachite and more than half of the strains produced oil that was fluorescent. Preliminary studies suggest that these pigments are likely a result of contamination by melanin, melanin breakdown products, and melanin intermediates, which are common pigments associated with *A. pullulans*. The oils have demonstrated biosurfactant properties (Manitchotpisit, et al. (2011)). Additionally, it has been shown that oil from different strains differentially inhibits mammalian cancer cell lines (Manitchotpisit, et al. (2014)). Recently, these microbial oils have been demonstrated to exhibit potent selective antibacterial activities against certain Streptococcal species (Bischoff, et al., *J. Antibiot.*, (2015) 68:642-45).

The antibacterial activities of these microbial oils (also termed "liamocins") may have potential applications, similar to other glycolipids or *A. pullulans* secreted metabolites, as a veterinary treatment (Cortes-Sanchez, et al., *Microbiol. Res.*, 168(1):22-32 (2013)), an antifouling agent (Gao, et al., *Marine Poll. Bull.*, 77(1-2):172-6 (2013); Abdel-Lateff, et al., *Nat. Prod. Commns.*, 4(3):389-94 (2009)), and a phytopathogen control agent (Le Dang, et al., *J. Agr. Food Chem.*, 62(15):3363-70 (2014)). In addition, the medium-chain dihydroxydecanoate fatty acid is promising as a potential chemical feedstock for the synthesis of a wide variety of commercially relevant products, such as biosurfactants and polymers (Tang, et al., *Polymer Chem.*, 5(9):3231-37 (2014); Schneiderman, et al., *J. Chem. Edu.*, 91(1); 131-5 (2014).

*A. pullulans* is also used for production the antibiotic aureobasidin and $\beta$-glucan. Production of both of these products could be improved by utilizing strains that are no longer producing melanin or melanin-related pigments. In addition, *A. pullulans* was recently shown to produce significant amounts of intracellular lipids (Wang et al., *Process Biochem.*, 49(5):725-31 (2014)), which may have potential for biodiesel or specialty oil production (Sitepu et al., *Biotech. Adv.*, 32(7):1336-1360 (2014)).

As alluded to above, one of the problems with using *A. pullulans* for bioproduct formation is that most strains produce dark melanin-associated pigments that contaminate the final desired product. These contaminating pigments can be removed by treatment with activated charcoal or hydrogen peroxide, but further purification with ultrafiltration and ion exchange resins are typically required. These clean up steps frequently result in loss of the desired bioproduct and add further cost to the manufacturing process (Mishra and Vuppu, *Res. J. Microbiol. Biotech.*, 2:16-19 (2013); Leathers, *Appl. Microbiol. Biotech.*, 62(5-6):468-473 (2003)). Oils and other bioproducts free of melanin or melanin-related pigments would be easier and cheaper to purify, making them more valuable and more economically feasible to produce. Thus, downstream products, such as biodiesel and food additives and preservatives would also be cheaper to produce.

Therefore, it is an object of the present invention to provide methods and strains of *A. pullulans* for the production of desired bioproducts as well as melanin-free bioproducts. Using the strains and methodologies presented here provides not only for a cheaper alternative to the use of non-modified strains, but also allows for a more ecologically responsible approach for the production of some bioproducts.

SUMMARY OF THE INVENTION

One aspect of the present invention is providing a biologically pure strain lacking mannitol-1-phosphate-dehydrogenase activity. In one instance, the biologically pure strain is the *A. pullulans* strain MpdKO.

An additional aspect of the invention disclosed herein is providing a biologically pure strain lacking mannitol-dehydrogenase activity. In one instance, the biologically pure strain is the *A. pullulans* strain Mdh2KO.

It is another object of the invention disclosed herein to provide a biologically pure strain lacking polyketide-synthase activity. In one instance, the biologically pure strain is the *A. pullulans* strain PksKO.

Further provided herein is a method of producing arabitol-liamocins, comprising the steps of: a) growing a culture of *A. pullulans* comprising a biologically pure strain lacking a functional MPD1 gene under conditions sufficient to support the production of arabitol-liamocins, such as growth media having a substantial absence of arabitol; and b) collecting the arabitol-liamocins from at least part of the culture, thereby producing arabitol-liamocins. In some embodiments, the biologically pure strain is the deposited strain NRRL 67079. In still other embodiments, the growth medium contains glucose as the sole carbon source.

An additional embodiment provided herein is a method of producing one or more bioproducts, comprising the steps of: growing a culture of *A. pullulans* comprising a biologically pure strain lacking a functional MDH2 gene and lacking a functional MPD1 gene under conditions sufficient to support the production of one or more bioproducts including liamocins and exophilins; and collecting one or more of the bioproducts from at least part of the culture, thereby producing the bioproduct. In some embodiments of this methodology, the growth of the culture occurs in or on a growth medium containing glucose or fructose as the sole carbon source. In specific embodiments, the bioproduct is an exophilin. In other embodiments, the bioproduct is a liamocin with a lactose, glucose, mannose, galactose, arabinose, xylose, glucitol, galactitol, xylitol, ribitol, threitol, erythritol, or glycerol head group. In still another embodiment, the bioproduct is a fructose-liamocin (a liamocin with a fructose head group).

Another invention detailed herein is a method of producing *massoia* lactone from a culture of *A. pullulans*, comprising the steps of: growing a culture of *A. pullulans* comprising a biologically pure strain lacking a functional PKS gene under conditions sufficient to support the production of *massoia* lactone; and b) collecting the *massoia* lactone from at least part of the culture, thereby producing *massoia* lactone. In a particular embodiment, the biologically pure strain utilized in practicing this methodology is the deposited strain NRRL 67080.

In yet another embodiment of the invention, this application discloses a method of producing a substantially melanin-free bioproduct from a culture of *A. pullulans*, comprising the steps of: a) growing a culture of *A. pullulans* comprising a biologically pure strain lacking a functional PKS4 gene under conditions sufficient to support the production of the bioproduct; and b) collecting the bioproduct from at least part of the culture, thereby producing a substantially melanin-free bioproduct. In some instances the bioproduct produced is one or more of pullulan, a liamocin, a lactone, an exophilin, poly(β-malic acid), β-glucan, aureobasidin, an intracellular fatty acid, and a triacylglycerol. In specific embodiments, the bioproduct is a liamocin, such as those with a head group comprised of lactose, glucose, mannose, galactose, arabinose, xylose, glucitol, galactitol, xylitol, ribitol, threitol, erythritol, or glycerol. In other embodiments, the bioproduct is *massoia* lactone. This methodology can be practiced using the biologically pure deposited strain NRRL 67080.

Also provided herein are compositions containing the novel fructose-liamocin (liamocin with a fructose head group). Such fructose-liamocins can be produced utilizing a biologically pure *A. pullulans* strain lacking a functional MDH2 gene and lacking a functional MPD1 gene.

Incorporation by Reference

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

STATEMENT OF DEPOSIT

Figure 1:
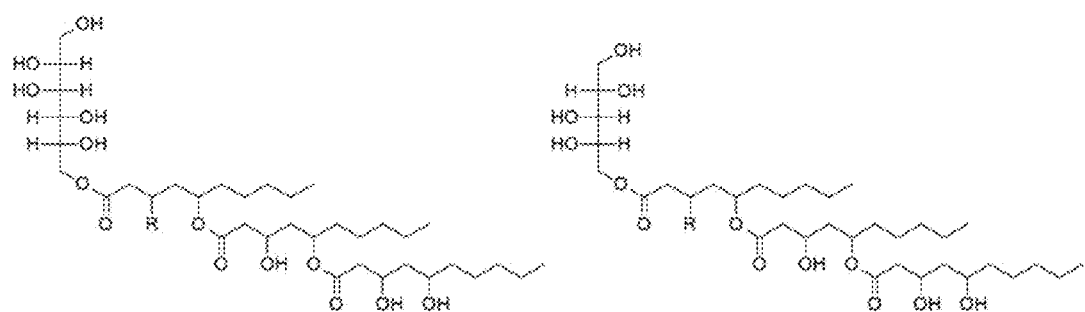
FIG. 1 provides an example of liamocin structures. Man-A2 (left) contains three 0-linked 3,5-dihydroxydecanoate groups with a mannitol headgroup. Ara-A2 (right) contains an arabitol headgroup. R=OH or O-acetyl. A2 defines the R group as 0-acetyl.

Strains representative of the inventions disclosed herein were deposited on Aug. 6, 2015 under the terms of the Budapest Treaty with the Agricultural Research Service (ARS) Patent Culture Collection. A representative *A. pullulans* Mpd1KO strain (a strain with a disrupted MPD1 gene (SEQ ID NO. 1)) was deposited under ARS Patent Culture Collection Reference No. NRRL 67079 and lacks a functional MPD1 gene. A representative *A. pullulans* Psk4KO strain (a strain with a disrupted PSK4 gene (SEQ ID NO. 4)) was deposited under ARS Patent Culture Collection Reference No. NRRL 67080 and lacks a functional PSK4 gene. Strains representative of the inventions disclosed herein were also deposited on Jul. 12, 2016 under the terms of the Budapest Treaty with the Agricultural Research Service (ARS) Patent Culture Collection. A representative *A. pullulans* Mdh2KO/Mpd1KO strain (a strain with a disrupted MPD1 gene (SEQ ID NO. 1) and a disrupted MDH2 gene (SEQ ID NO. 3)) was deposited under ARS Patent Culture Collection Reference No. NRRL 67281 and lacks a functional MPD1 gene and a functional MDH2 gene. A representative *A. pullulans* Mdh2KO strain (a strain with a disrupted MDH2 gene (SEQ ID NO. 3) was deposited under ARS Patent Culture Collection Reference No. NRRL 67282 and lacks a functional MDH2 gene. The microorganism deposits were made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any *A. pullulans* strains having the identifying characteristics of NRRL 67079, NRRL 67080, NRRL 67281, or NRRL 67282, including subcultures and variants thereof which have the identifying characteristics and activity as described herein are included.

DETAILED DESCRIPTION OF THE INVENTION

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This invention teaches methods and describes tools for producing genetically altered strains of *A. pullulans*.

As used in the specification and claims, use of the singular "a", "an", and "the" include plural references unless the context clearly dictates otherwise.

The term "*A. pullulans*" refers to *Aureobasidium pullulans*.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g.

The phrases "substantially free of melanin," "substantially melanin-free," or other grammatical variations thereof refer to cultures, media, bioproducts, etc. which contain no detectable melanin produced by the same microorganism producing a bioproduct of interest prior to any downstream process which would remove melanin. These phrases also refer to cultures, media, bioproducts, etc. to which melanin is added from an exogenous source, but which otherwise meet the definition above.

The phrases "substantially free of arabitol," "substantially arabitol-free," or other grammatical variations thereof refer to cultures, media, etc., which contain no arabitol, or contain insufficient arabitol (when viewed as a sole carbon source) to support more than three doubling times of a microbe producing a desired bioproduct.

The terms MPD and MPD1 are defined as the gene encoding mannitol-1-phosphate-dehydrogenase in *A. pullulans*. (SEQ ID NO. 1)

The term MDH1 is defined as the gene encoding a putative mannitol dehydrogenase in *A. pullulans* that is likely a mitochondrial enzyme (cytochrome) mainly involved in converting mannitol to fructose. (SEQ ID NO. 2)

The term MDH2 is defined as the gene encoding mannitol-dehydrogenase in *A. pullulans*. (SEQ ID NO. 3)

The terms PKS and PKS4 are defined as the gene encoding polyketide synthase in *A. pullulans*. (SEQ ID NO. 4)

The term URA3 is defined as the gene encoding Orotidine-5'-phosphate (OMP) decarboxylase in *A. pullulans*. (SEQ ID NO. 5)

The terms "MpdKO", "Mpd1KO", "Mdh1KO", "Mdh2KO", "PksKO", "Psk4KO", and grammatical variations thereof, refer to strains of *A. pullulans* which lack the functional indicated gene because of targeted genetic disruption of the indicated gene. These terms can be used in combination to refer to strains with multiple disrupted genes, e.g., "Mdh2KO/Mpd1KO" refers to a strain in which both the MDH2 and MPD1 genes have been disrupted. These terms can also be used to identify the specific genetically disrupted strains described herein—for example "MpdKO" can refer to an *A. pullulans* strain in which the MPD1 gene has been disrupted with the cassette of SEQ ID NO. 6 and "PksKO" can refer to an *A. pullulans* strain in which the PKS4 gene has been disrupted with the cassette of SEQ ID NO. 7.

Some embodiments of the present invention involve creating strains which lack a functional gene. As used herein, the phrase "strains lacking a functional gene", and grammatical variations thereof, refers to a microbial strain in which the referenced gene has been mutated, deleted, or otherwise modified such that the gene no longer produces a functional protein. Thus, the phrase includes mutational, insertional and deletional variants of the subject gene. Such variants can include alteration of transcriptional regulatory machinery, translational regulatory machinery, coding regions and non-coding regions. Non-limiting examples of such changes include insertion of point mutations, insertions or deletions causing frame shift mutations, deletions of some or all of the coding sequence, alterations rendering promoters or start codons inoperable, and alterations rendering stop codons inoperable. Additionally, introduction of genetic elements that interfere with translation, but do not directly affect the target gene itself (e.g., introduction of anti-sense RNA encoding plasmids or other genetic elements) are also included. Those skilled in the art will readily recognize methodologies capable of producing strains lacking a functional gene.

Mutational, insertional, and deletional variants of the disclosed nucleotide sequences and genes can be readily prepared by methods which are well known to those skilled in the art. It is well within the skill of a person trained in this art to make mutational, insertional, and deletional mutations which are equivalent in function to the specific ones disclosed herein.

In some embodiments, strains of *A. pullulans* are genetically modified to deplete the strain of the capacity to produce a particular biosynthetic enzyme. In other embodiments, strains of *A. pullulans* are genetically modified to deplete the strain of the capacity to produce more than one biosynthetic enzyme. In some embodiments, depleting the capacity of a strain of *A. pullulans* to produce one or more biosynthetic enzymes results in a biochemical alteration in the resulting strain leading to production of a desired bioproduct. In still other embodiments, depleting the capacity of a strain of *A. pullulans* to produce a biosynthetic enzyme prevents that strain from producing an unwanted or undesirable biocontaminant that would otherwise be co-produced along with a desired bioproduct. The discussion below provides techniques that can be used to produce genetically modified strains of *A. pullulans*. The discussion is not limiting in any way on the scope of the inventions disclosed herein, and any current or future techniques which allow for the production of such strains by one of skill in the art can be utilized. Following the teachings herein and using knowledge and techniques well known in the art, the skilled worker will be able to make a large number of operative embodiments having equivalent functionality to those listed and contemplated herein.

Molecular Biological Methods

An isolated nucleic acid is a nucleic acid the structure of which is not identical to that of any naturally occurring nucleic acid. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

The term recombinant nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Recombinant host cells, in the present context, are those which have been genetically modified to contain an isolated nucleic molecule of the instant invention. The nucleic acid can be introduced by any means known to the art which is appropriate for the particular type of cell, including without limitation, transformation, lipofection, electroporation or any other methodology known by those skilled in the art.

In practicing some embodiments of the invention disclosed herein, it is useful to modify the genomic DNA of a strain of *A. pullulans* or another target organism. In many embodiments, such modification involves deletion of all or a portion of a target gene, including but not limited to the open reading frame of the target gene, transcriptional regulators such as promoters of the target gene, and any other regulatory nucleic acid sequences positioned 5' or 3' from the open reading frame. Such deletional mutations can be achieved using any technique known to those of skill in the art. One such approach is to utilize a "deletion cassette" or "knockout cassette" (See, e.g., Fonzi and Irwin, *Genetics*, 134(3):717-28 (1993)). Knockout cassettes typically comprise at least three nucleic acid components: 1) an isolated nucleic acid that is homologous to a 5' region of a target gene or other locus; 2) an isolated nucleic acid that serves as a marker; and 3) an isolated nucleic acid that his homologous to a 3'region of a target gene or other locus. Other genetic elements can be included, depending on the particular application and design of the cassette. A knockout cassette is then introduced into an organism of interest via any appropriate means known in the art (e.g., electroporation). Taking advantage of intracellular processes such as homologous recombination, the knockout cassette integrates into the genome of the target cell. In some instances, this initial integration event deletes all or part of the target gene or locus replacing the wild type genomic DNA and deleting or "knocking out" the wild type DNA between the 5' and 3' nucleic acids of the knockout cassette. In other instances, the initial integration of the knockout cassette is followed by a subsequent recombinatorial event that results in the deletion of the target gene or locus, such as by introducing heterologous DNA flanking the gene or locus of interest and inducing homologous recombination between the two heterologous DNA segments. Knockout cassettes can be constructed in a variety of ways known in the art (e.g., split marker transformation). Knockout cassettes can contain multiple markers that allow one skilled in the art to detect initial integration events and subsequent recombinatorial events.

Where a recombinant nucleic acid is intended for expression, cloning, or replication of a particular sequence, DNA constructs prepared for introduction into a prokaryotic or eukaryotic host will typically comprise a replication system (i.e. vector) recognized by the host, including the intended DNA fragment encoding the desired polypeptide, and can also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

In some instances, a host cell other than *A. pullulans* can serve as a recipient for recombinant DNA. For example, a bacterial host may be utilized to clone a plasmid in which a deletion cassette is constructed, replicated, or analyzed. In such instances, a recombinant DNA fragment may require an appropriate promoter and other necessary vector sequences that can be readily selected so as to be functional in the host. Examples of workable combinations of cell lines and expression vectors are described in Sambrook et al. (1989) vide infra; Ausubel et al. (Eds.) (1995) *Current Protocols in Molecular Biology*, Greene Publishing and Wiley Interscience, New York; and Metzger et al. (1988) *Nature*, 334: 31-36. Many useful vectors for expression in bacteria, yeast, fungal, mammalian, insect, plant or other cells are well known in the art and may be obtained from commercial vendors or constructed de novo.

Knockout cassettes, vectors and other nucleic acids introduced into a host cell will likely contain a selectable marker, that is, a gene encoding a protein necessary for the survival or growth of a host cell transformed with the nucleic acid. Although such a marker gene may be carried on another polynucleotide sequence co-introduced into the host cell, it is most often contained on the transforming nucleic acid. Only those host cells into which the marker gene has been introduced will survive and/or grow under selective conditions. Typical selection genes encode proteins that (a) confer resistance to antibiotics or other toxic substances, e.g., hygromycin, ampicillin, neomycin, methotrexate, etc.; (b) complement auxotrophic deficiencies; or (c) supply critical nutrients not available from complex media. The choice of the proper selectable marker will depend on the host cell and appropriate markers for different hosts are well known in the art.

Selectable markers useful in practicing the methodologies of the invention disclosed herein can be "positive selectable markers". Typically, positive selection refers to the case in which a genetically altered cell can survive in the presence of a toxic substance only if the recombinant polynucleotide of interest is present within the cell. For example, when a recombinant deletion cassette introduced into a cell contains a hygromycin B resistance gene, only those transformants containing the recombinant polynucleotide will survive when grown in the presence of hygromycin B. Other positive markers include, but are not limited to, mutated beta-tubulin (ben) gene, which confers resistance to benomyl; Bar, which confers resistance to phosphinothricin; Ble, which confers resistance to phleomycin; Sat-1, which confers resistance to nourseothricin, and cbx, conferring resistance to carboxin. Genes essential for the synthesis of an essential nutrient (such as amino acid arginine and nucleoside pyrimidine) may also be used as positive selection markers and are contemplated by the present invention. Negative selectable markers and screenable markers are also well known in the art and are contemplated by the present invention.

Screening and molecular analysis of recombinant strains of the present invention can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) *Current Protocols in Molecular Biology*, John Wiley & Sons, NY, N.Y., for further guidance on hybridization conditions.

Additionally, screening and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) *Science* 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Hybridization-based screening of genetically altered strains typically utilizes homologous nucleic acid probes with homology to a target nucleic acid to be detected. The extent of homology between a probe and a target nucleic acid can be varied according to the particular application. Homology can be 50%-100%. In some instances, such homology is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See www.ncbi.nih.gov.

Preferred host cells are members of the genus *Aureobasidium*, especially *A. pullulans*. Filamentous fungi such as members of the genera *Aspergillus, Trichoderma, Penicillium*, etc. are also useful host organisms for expression of the DNA of this invention. (Van den Handel, C. et al. (1991) In: Bennett, J. W. and Lasure, L. L. (eds.), *More Gene Manipulations in Fungi*, Academic Press, Inc., New York, 397-428). Yeasts such as *Saccharomyces cerevisiae, Candida albicans, Candida glabrata*, and *Cryptococcus neoformans*, etc. are also useful host organisms.

Microbial Cultures

*Aureobasidium pullulans* is a ubiquitous fungus commonly found in samples of soil, water, air and decaying plant material. Isolates of *A. pullulans* exhibit polymorphic forms ranging from blastic conidia and swollen cells to pseudohyphae, hyphae, and chlamydospores, depending on isolate differences, age, medium and culture conditions (Cooke, *Mycopathologia*, 12:1-45 (1959); Leathers, Polysaccharides from eukaryotes. In: Vandamme, E. J., De Baets, S., and Steinbuchel, A., Editors. Biopolymers. Weinheim, Germany: Wiley-VCH. p. 1-35 (2002)). Most strains produce dark pigments (melanin) and pullulan, an exopolysaccharide that, in older cultures can lead to increased culture viscosity. Like most fungi, culture conditions under which *A. pullulans* is grown, affect multiple aspects of the biology of the organism, including morphological form and bioproduct spectrum.

Thus, one of skill in the art will recognize that multiple culture conditions can be modified in practicing the invention disclosed herein. Non-limiting examples of culture conditions that can be modified during the application and practice of the inventions disclosed herein, include: 1) temperature; 2) primary carbon source; 3) oxygen concentration; 4) primary nitrogen source; 5) pH; 6) mineral and other ion concentration; 7) age/growth phase of culture; 8) organization of an industrial fermenter; and 9) predominant morphological form. One of skill in the art will recognize that other culture parameters affecting desired bioproduct production and bioproduct yield can be modified.

In one aspect of the invention, cultures of *A. pullulans* strains described herein can be grown at any temperature that facilitates the production of one or more bioproducts. For example, a culture can be grown at a temperature of 15°–30° C., or any whole or partial degree within that range, including, but not limited to 15.0° C., 15.5° C., 16.0° C., 16.5° C., 17.0° C., 17.5° C., 18.0° C., 18.5° C., 19.0° C., 19.5° C., 20.0° C., 20.5° C., 21.0° C., 21.5° C., 22.0° C., 22.5° C., 23.0° C., 23.5° C., 24.0° C., 24.5° C., 25.0° C., 25.5° C., 26.0° C., 26.5° C., 27.0° C., 27.5° C., 28.0° C., 28.5° C., 29.0° C., 29.5° C., and 30.0° C.

In some embodiments, the microbial strains described herein can be grown under conditions where the pH of the culture facilitates the production of one or more bioproducts of interest. For example, a culture can be grown in media where the pH is between 5.5 and 8.5, 6.0 and 7.5, or any value within that range, including, but not limited to pH 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5. One of skill in the art will recognize that a stable pH does not need to be maintained throughout the entirety of the growth of the strain producing the bioproduct(s) of interest. Thus, in some embodiments, the pH of a microbial culture of the present invention will vary. In other embodiments, pH buffers can be added to maintain a relatively stable pH where the pH of the culture medium over the life of the culture does not vary from a chosen starting point by more than ±0.5.

In some embodiments, microbial strains of the present invention can be grown in the presence of particular carbon sources. For example, a culture can be grown in the presence of simple carbon sources such as (D- or L-) arabitol, sucrose, fructose, glucose, mannose, galactose, arabinose, arabinose, xylose, mannitol, glucitol, galactitol, xylitol, ribitol, threitol, glycerol, gluconic acid, glucosamine, or meso-erythritol. Alternately, a culture can be grown in the presence of complex carbon sources such as cellulose, starch, beet molasses, carob pod, cornmeal hydrolysates, corn syrup, fuel ethanol fermentation stillage, grape skin pulp, vegetable oils, peat hydrolysate, hydrolyzed potato starch, and spent sulfite liquor. Carbon sources that are also sources for other nutritional requirements, such as nitrogen, can be utilized. For example, media for use in the present invention can include amino acids such as aspartate, threonine, lysine, methionine, isoleucine, asparagine, glutamic acid, glutamine, proline, alanine, valine, leucine, tryptophan, tyrosine, phenylalanine and their metabolic intermediates. These lists are non-limiting and it is well within the capabilities of one of skill in the art to utilize other carbon sources in practicing the present invention. Any carbon source can be used alone or in combination with other carbon sources.

Other nutritional parameters can also be varied, including nitrogen sources. Non-limiting examples of nitrogen sources include organic nitrogen sources (e.g., peptone, soybean pomace, yeast extract, food gravy, malt extract, corn steep liquor and soybean flour) and inorganic nitrogen sources (e.g, urea, ammonium sulfate, ammonium chloride, ammonium phosphate, ammonium carbonate and ammonium nitrate) can be included in growth media utilized in the practice of the present invention. Phosphate sources such as potassium dihydrogen phosphate, dipotassium hydrogen phosphate and their corresponding sodium-containing salts can be included in growth media as necessary. Metal and mineral salts such as salts of zinc, iron, magnesium, manganese, calcium and copper can be included as needed. Other nutritional supplements, such as vitamins (e.g, biotin, thiamine) can also be included. One of skill in the art will recognize that varying culture nutritional makeup can be utilized to maximize production of a bioproduct of interest and decrease production of undesired by-products. Any of these nutrients can be used alone or in combination with any other nutrient.

Nutrients can be added to the culture in any feeding regimen, including, but not limited to high cell-density culture, batch culture, fed-batch culture, constantly-fed-batch culture, exponentially-fed batch culture, continuous culture, or a mixture of these approaches for different nutrients.

In some instances, the length of time a culture is grown can be modified to enhance or begin production of a bioproduct of interest. For example, a culture can be grown for 10-300 hours, or more, or any time point within that range, for example 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 hours, or more before harvesting of a bioproduct commences.

Additionally, optimization of bioproduct production can depend on growing a culture to a particular point in the life cycle. For example, a culture can be grown to early lag phase, middle lag phase, late lag phase, early exponential phase, mid-exponential phase, late exponential phase, early stationary phase, mid-stationary phase, or death phase. In some instances, cultures can be maintained in a growth phase (e.g., by fed-batch culture) in order to maintain a particular growth phase for the culture.

In other instances, culture conditions can be altered so that one morphological form of $A.$ $pullulans$ strains utilized to produce bioproduct(s) of interest predominates over other morphological forms. For example, culture conditions can be controlled so that yeast-like forms predominate, chlamydospores predominate, or hyphae/pseudohyphae predominate.

$A.$ $pullulans$ demonstrates strain-specific differences in bioproduct production and bioproduct production levels. Thus, in practicing the methodologies taught herein, a strain can be selected that already produces a bioproduct of interest, or produces a bioproduct of interest at a relatively higher level than other strains. One of skill in the art would be able to utilize the genetic alteration techniques described herein to produce an altered $A.$ $pullulans$ strain of differing genotypic/phenotypic backgrounds. Additionally, the approaches provided herein can be utilized to produce genetically altered species of the genus $Aureobasidium$ other than $A.$ $pullulans$ that produce bioproducts of interest.

Bioproduct Extraction from Cultures

To utilize a bioproduct for downstream purposes (e.g., biofuel production or for use as a food additive), it may be necessary to extract the bioproduct of interest from the microbial culture. Given that bioproducts can comprise different chemical compounds with varying chemical properties, one of skill in the art will recognize that different approaches to isolate or purify a bioproduct from a microbial culture will necessarily need to be appropriate for that bioproduct.

$A.$ $pullulans$ produces numerous important bioproducts, including, but not limited to liamocins, pullulan, poly (β-malic acid), β-glucan, aureobasidin, and intracellular fatty acids or triacylglycerols. Although not all of these products are produced by every strain, many of these products are synthesized by $A.$ $pullulans$ NRRL 50384, however, the invention disclosed herein could be utilized with numerous other microorganisms as previously described. The technology for producing and isolating most $Aureobasidium$ bioproducts are fairly well established, but alternative purification methods can be used depending on the desired applications. One of skill in the art will recognize that the following examples of extraction methodologies are provided as examples and are not meant to be limiting on the procedures that can be utilized to practice the invention disclosed herein.

Pullulan and poly(β-L-malic acid) (PMA) are predominantly extracellular and isolated from cell-free culture supernatants. Pullulan and PMA are water soluble, thus are typically isolated from cultures by collecting supernatants and precipitating the bioproducts. One approach to isolating these products was described by Manitchotpisit et al. (ibid., 2012). Cells were removed by centrifugation at 10,000×g for 20 min. The culture supernatants were adjusted to pH 5.0 by the dropwise addition of 30% (w/v) $CaCO_3$. Pullulan was precipitated by the addition of one volume of 95% ethanol followed by centrifugation at 16,900×g for 30 min. PMA was then precipitated by the addition of an additional volume of 95% ethanol, followed by incubation at 4° C. overnight and centrifugation at 16,900×g for 30 min. Precipitated PMA was dissolved in 200 mL of purified water and lyophilized. Any other isolation methodology appropriate for these bioproducts can be utilized.

Liamocins are typically extracellular and can be separated by centrifugation and purified through solvent extraction. The following example is from Manitchotpisit et al. (ibid. 2011). Approximately 50 ml of cells and heavy oil were removed by centrifugation at 10,000×g for 20 min. Extracellular heavy oil appeared as a layer beneath the precipitated cells. Cells were gently resuspended in 3-5 ml of distilled water and transferred to a screw-cap glass tube (13 mm×100 mm). Culture flasks and centrifuge bottles were washed with 3-5 ml of methyl ethyl ketone and heavy oil was dissolved in this solvent. The dissolved oil was recombined with the resuspended cells and the mixture was vortexed vigorously and allowed to separate overnight at room temperature. The aqueous and extracted cell layers were then removed, and the solvent was evaporated from the oil overnight under a stream of air. Alternatively, whole cultures were extracted with at least 50 ml of methyl ethyl ketone, and solvent, aqueous, and biomass layers were isolated in a separatory funnel. The whole culture method is simpler but requires more solvent and more time for solvent evaporation.

A number of studies describe additional (non-pullulan) polysaccharides, typically water-soluble extracellular polysaccharides, including certain β-glucans, from certain strains and mutants of $A.$ $pullulans$ (Leathers, Polysaccharides from eukaryotes. In: Vandamme, E. J., De Baets, S., and Steinbuchel, A., Editors. Biopolymers. Weinheim, Germany: Wiley-VCH. p. 1-35 (2002)). A typical purification of β-glucans can involve removing cells by centrifugation or filtration, removing contaminants by adsorption with activated carbon, concentrating polysaccharides by ultrafiltration, and precipitating final product with 80% ethanol (Muramatsu, et al., $PLoS$ $One$, 7:(2012)).

Aureobasidins are typically extracellular and purified from a fermentation broth through solvent extraction and column purification. A typical purification could involve solubilizing aureobasidins in fermentation broth with an equal volume of ethanol, separating on an adsorption column (e.g., a Diaion HP-40 column) equilibrated with 50% ethanol and eluted with 95% ethanol, diluting elute twice with water and further separating on reverse phase ODS-W (Soken ODS-W from Soken Chemicals Co.) equilibrated with 40% ethanol and eluted with 60% ethanol (Yoshikawa, et al., $J.$ $Antibiotics$ (Tokyo), 46:1347-54 (1993)).

Triacylglycerol or triglycerides are typically intracellular and removed from cells through solvent extraction. A number of different solvent extraction methods allow preferential solubilization of the desired lipid (Christie, Advances in Lipid Methodology, 5:97-115 (2003)). These solvent extraction methods can be utilized with dried (i.e., lyophilized, oven) cultures or cells that have been lysed through mechanical, chemical, or enzymatic processes (Yu, et al., Eur. J Lipid Sci. Tech., 117:730-737 (2015)). A typical extraction method for A. pullulans would involve collecting cells through centrifugation, washing with saline, drying at 80° C., and homogenizing cells with 2:1 chloroform-methanol mixture.

Massoia lactone production by A. pullulans has never been reported or demonstrated prior to our construction of a strain lacking a functional PKS gene. During analysis of that knockout strain, we discovered that massoia lactone can be found in the extracellular liamocin fractions and intracellularly for A. pullulans. Massoia lactone can be separated directly from liamocins by butan-2-one:chloroform:water (1:2:2 by volume) partitioning. Alternatively, massoia lactone can be extracted from lysed cells of this knockout strain using chloroform:methanol (1:1) or acetone:ethyl acetate (1:1), but further purification is required.

Bioproducts and Uses

In practicing the present invention, it will be recognized by one of skill in the art that any of the disclosed strains can be utilized to produce a bioproduct of interest. In some instances, an A. pullulans strain lacking at least one gene encoding a mannitol biosynthetic enzyme (See, FIG. 2) can be utilized to produce a bioproduct of interest. In some embodiments, the present invention can be practiced using an A. pullulans strain lacking a functional mannitol-1-phosphate-dehydrogenase-encoding (MPD1) gene (SEQ ID NO. 1) to produce a bioproduct of interest. In another embodiment, the present invention can be practiced using an A. pullulans strain lacking a functional mannitol-dehydrogenase-encoding (MDH2) gene (SEQ ID NO. 3) to produce a bioproduct of interest. In another embodiment, the present invention can be practiced using an A. pullulans strain lacking a functional polyketide-synthase-encoding (PKS) gene (SEQ ID NO. 4) to produce a bioproduct of interest. In some embodiments, the present invention can be practiced using an A. pullulans strain lacking a functional putative-mannitol-dehydrogenase-encoding (MDH1) gene (SEQ ID NO. 2) to produce a bioproduct of interest. In still another embodiment, the present invention can be practiced using an A. pullulans strain lacking a functional MPD1 gene and lacking a functional PKS gene to produce a bioproduct of interest. In still another embodiment, the present invention can be practiced using an A. pullulans strain lacking a functional MDH2 gene as well as lacking a functional PKS gene to produce a bioproduct of interest, while not producing melanin. In still another embodiment, the present invention can be practiced using an A. pullulans strain lacking a functional MPD1 gene, lacking a functional MDH2 gene, and lacking a functional PKS gene to produce a bioproduct of interest, while not producing melanin. In particular embodiments, one of the strains described in the Examples section can be utilized to produce a bioproduct of interest. In other embodiments, the present invention can be practiced using an A. pullulans strain lacking a functional copy of a combination of any or all genes (MDH1, MDH2, MPD1, PKS) described herein.

Liamocins

Experiments utilizing Matrix-Assisted Laser Desorption/Ionization Mass Spectrometry (MALDI-TOF MS) spectra suggested that extracellular oil produced by A. pullulans oil contained a family of related oil structures. The structure of several of the oil components (termed "liamocins") from A. pullulans strain NRRL 50380 have previously been elucidated (Price et al., Carbohyd. Res., 370:24-32 (2013)). The liamocins identified to date are comprised of a polyol head group (either mannitol, arabitol, or glycerol) that is ester-linked at one end to a highly unusual fatty acid, 3,5-dihydroxydecanoic acid (FIG. 1). These 3,5-dihydroxydecanoic acid groups are themselves joined by 1,5-linked ester bonds, so that the liamocins form either A, B, or C-type that contain three, four, or five 3,5-dihydroxydecanoic acid groups, respectively. In addition, some liamocins contain a single 3'-O-acetyl group at the free 3-hydroxy position on the 3,5-dihydroxydecanoic fatty acid chain. Liamocins A1 and B1 are non-acetylated, whereas A2 and B2 each contain a single acetyl group.

Analysis of numerous liamocin-producing A. pullulans isolates grown under varying conditions reveal that liamocin trimers with a mannitol headgroup (e.g., Man-A1, Man-A2) are usually the predominant structure when glucose, fructose, sucrose, or xylose are used as the carbon source. Some A. pullulans strains have been identified that produced liamocins that were approximately 40% arabitol-containing structure (e.g., Ara-A1, Ara-A2, Ara-B1) when grown on glucose. Prior to the inventions disclosed herein, however, 100% arabitol-containing liamocin structures could only be produced by growing cells using arabitol as the sole carbon source. This method likely would be cost-prohibitive for many applications because of the relative expense of arabitol compared with glucose. Additionally, separating mixed liamocin structures (e.g., combinations of mannitol-liamocin and arabitol-liamocin) is technically very difficult. Thus, the strains and methodologies disclosed herein that modify the synthesis and/or accumulation of intracellular polyols in genetically altered Aureobasidium strains of the present invention would be valuable as a method to alter the chemical structures of the liamocins and to decrease unwanted polyol synthesis as contaminants of other bioproducts of interest.

Thus, in one embodiment, arabitol-liamocins can be produced utilizing an A. pullulans strain of the invention when grown in the absence of arabitol as a carbon source. In some embodiments, the A. pullulans strain utilized to produce arabitol-liamocins lacks at least one gene in a mannitol biosynthetic pathway. In other embodiments, an A. pullulans strain lacking a functional gene encoding mannitol-1-phosphate dehydrogenase (MPD1) has been is utilized to produce arabitol-liamocins. In still another embodiment, an A. pullulans strain lacking a functional MPD1 gene and lacking a functional MDH2 gene is utilized to produce arabitol-liamocins.

For example, any strains lacking one or more genes encoding for any protein necessary for mannitol production can be grown in the presence of D-fructose, D-glucose, D-mannose, D-galactose, D-arabinose, L-arabinose, D-xylose, D-mannitol, D-glucitol, D-galactitol, D-xylitol, D-ribitol, D-threitol, L-threitol, D-glycerol, or meso-erythritol. One of skill in the art will recognize that this list of carbon sources is not exclusive and that any carbon source that results in production of the desired bioproduct can be utilized. In a particular embodiment, the inexpensive carbon source, D-glucose can be utilized to produce arabitol-liamocins utilizing any the strains of this invention. In another particular embodiment, arabitol-liamocins are produced utilizing any of the knockout strains described in the Examples below.

In still other embodiments of the present invention, A. pullulans strains lacking at least one gene encoding a mannitol biosynthetic enzyme as well as lacking a gene encoding polyketide synthase (PKS) are used to produce liamocins that are melanin-free. In one embodiment, a strain used to produce melanin-free liamocins lacks a functional MPD1 gene and lacks a functional PKS gene. In another embodiment, a strain used to produce melanin-free liamocins lacks a functional MDH2 gene and lacks a functional PKS gene. In still another embodiment, a strain used to produce melanin-free liamocins lacks a functional MPD1 gene, lacks a functional MDH2 gene, and lacks a functional PKS gene. In particular embodiments, a specific strain described in the Examples below can be utilized to produce arabitol-liamocins that are essentially free of melanin without the need to remove melanin.

Figure 13:
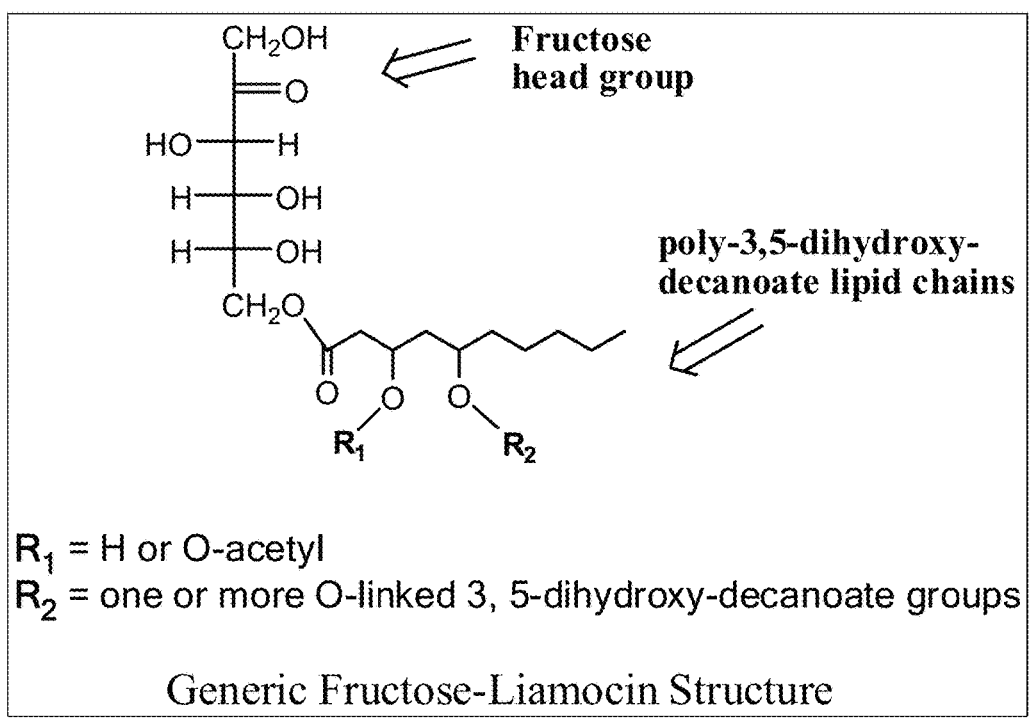
FIG. 13 provides a generic fructose-liamocin structure in which the fructose head group and the variable $R_1$ and $R_2$ groups are indicated.

The strains described herein comprising one or more genetic alterations can be used to produce a desired liamocin. In one embodiment, D- and/or L-mannitol liamocin A1, D- and/or L-mannitol liamocin A2, D- and/or L-mannitol liamocin B1, D- and/or L-mannitol liamocin B2, D- and/or L-mannitol liamocin C1, or D- and/or L-mannitol liamocin C2, or a combination thereof, can be produced as a bioproduct utilizing the strains of this invention. In another embodiment, D- and/or L-arabitol liamocin A1, D- and/or L-arabitol liamocin A2, D- and/or L-arabitol liamocin B1, D- and/or L-arabitol liamocin B2, D- and/or L-arabitol liamocin C1, or D- and/or L-arabitol liamocin C2, or a combination thereof, can be produced as a bioproduct utilizing the strains of this invention. In a third embodiment, 2-amino-D-mannitol liamocin A1, 2-amino-D-mannitol liamocin A2, 2-amino-D-mannitol liamocin B1, 2-amino-D-mannitol liamocin B2, 2-amino-D-mannitol liamocin C1, or 2-amino-D-mannitol liamocin C2, or a combination thereof, can be produced as a bioproduct utilizing the strains of this invention. In a fourth embodiment, 2-N-acetylamino-D-mannitol liamocin A1, 2-N-acetylamino-D-mannitol liamocin A2, 2-N-acetylamino-D-mannitol liamocin B1, 2-N-acetylamino-D-mannitol liamocin B2, 2-N-acetylamino-D-mannitol liamocin C1, or 2-N-acetylamino-D-mannitol liamocin C2, or a combination thereof, can be produced as a bioproduct utilizing the strains of this invention. In a fifth embodiment, D-fucitol liamocin A1, D-fucitol liamocin A2, D-fucitol liamocin B1, D-fucitol liamocin B2, D-fucitol liamocin C1, or D-fucitol liamocin C2, or a combination thereof can be used as the antibacterial compound of this invention. In a sixth embodiment, L-rhamnitol liamocin A1, L-rhamnitol liamocin A2, L-rhamnitol liamocin B1, L-rhamnitol liamocin B2, L-rhamnitol liamocin C1, L-rhamnitol liamocin C2, or a combination thereof can be produced as a bioproduct utilizing the strains of this invention. In a seventh embodiment, L-glycerol liamocin A1, L-glycerol liamocin A2, L-glycerol liamocin B1, L-glycerol liamocin B2, L-glycerol liamocin C1, L-glycerol liamocin C2, D-glycerol liamocin A1, D-glycerol liamocin A2, D-glycerol liamocin B1, D-glycerol liamocin B2, D-glycerol liamocin C1, D-glycerol liamocin C2, L-threitol liamocin A1, L-threitol liamocin A2, L-threitol liamocin B1, L-threitol liamocin B2, L-threitol liamocin C1, L-threitol liamocin C2, D-threitol liamocin A1, D-threitol liamocin A2, D-threitol liamocin B1, D-threitol liamocin B2, D-threitol liamocin C2, L-erythritol liamocin A1, L-erythritol liamocin A2, L-erythritol liamocin B1, L-erythritol liamocin B2, L-erythritol liamocin C1, L-erythritol liamocin C2, D-erythritol liamocin A1, D-erythritol liamocin A1, D-erythritol liamocin B1, D-erythritol liamocin B2, D-erythritol liamocin C1, D-erythritol liamocin C2, or a combination thereof can be produced as a bioproduct utilizing the strains of this invention. In still another embodiment, a fructose liamocin (FIG. 13) and exophilins can be produced by a strain of the present invention lacking functional MPD1 and MDH1 genes. In yet another embodiment, any combination of any of the compounds (glycerol-liamocins, threitol-liamoicins, erythritol-liamocins, mannitol-liamocins, arabitol-liamocins, 2-amino-D-mannitol liamocins, 2-N-acetylamino-D-mannitol liamocins, D-fucitol liamocins, fructose-liamocins and L-rhamnitol liamocins) mentioned in this paragraph can be produced as a bioproduct utilizing the strains of this invention.

In another embodiment, a liamocin produced is any of the compounds described in Formula 1 where $R_1$ is either, independently, $COCH_3$ or H; and $R_2$ is, independently, one or more O-linked 3,5-dihydroxy-decanoate groups; and $R_3$ is, independently, $C_xO_xH_{2x+1}$, such as one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol (also called sorbitol), L- or D-galactitol (also called dulcitol), L- or D-talitol, 2-amino-D-mannitol, 2N-acetylamino-D-mannitol, L-rhamnitol, or D-fucitol; individually or in combination with each other, can be produced as a bioproduct utilizing the strains of this invention. In still another embodiment, any or all of the above liamocins can be produced as a bioproduct by a strain of this invention that lacks the ability to produce melanin. Thus, in such embodiments, liamocins that are essentially free of melanin are produced by growing strains lacking a functional PKS gene under conditions sufficient to produce the desired liamocin. In a particular embodiment, a desired liamocin is produced by a PKS knockout strain produced by the methods described in the Examples below.

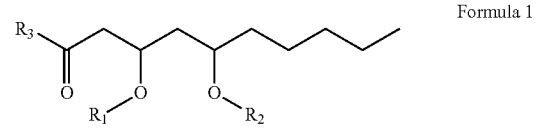

Formula 1

Pullulan

A well-established product of *A. pullulans* is the exopolysaccharide, pullulan. This complex polysaccharide is a linear homopolysaccharide of glucose that is often described as an α-(1→6) linked polymer of maltotriose subunits, however, other structures (such as the tetramer maltotetraose) may be present within a pullulan polymeric chain (Leathers, Polysaccharides from eukaryotes. In: Vandamme, E. J., De Baets, S., and Steinbuchel, A., Editors. Biopolymers. Weinheim, Germany: Wiley-VCH. p. 1-35 (2002)). Regular alternation of the (1→4) and (1→6) bonds results in two distinctive properties of this large molecule, namely, structural flexibility and enhanced solubility (Leathers, 1993). Pullulan also demonstrates adhesive properties and a capacity to form fibers, compression moldings and strong, oxygen-impermeable films. Chemical derivatization utilizing reactive groups can be used to alter the solubility (and other physiochemical properties) of pullulan. Pullulan is non-toxic, edible, and biodegradable, making it useful in a wide variety of industrial applications, pharmaceutical applications and food applications.

Pullulan is considered a dietary fiber in humans and provides few calories because it is resistant to mammalian amylases. Some studies indicate that it functions as a prebiotic, promoting the growth of beneficial bacteria. Pullulan can be incorporated in both solid and liquid foods, where it functions to achieve desired consistency, dispersability, moisture retention, and other parameters. It can be used as a replacement for starch in multiple food applications. It can also serve as a food preservative, as pullulan is not readily assimilated by the bacteria and fungi responsible for food spoilage. It has adhesive properties, making it useful as a binder and stabilizer in food pastes.

Films made of pullulan are clear, oxygen-permeable and dissolve readily in water, thus, these films readily melt in the mouth. One of the primary uses of such films is in the oral care industry, where pullulan film is impregnated with mouthwash or other oral hygiene products. Pullulan films can also be used as coating or packaging material for dried foods, or applied directly to food as a protective coating.

In the pharmaceutical industry, pullulan can be used as a coating or layer for tablets, pills, and granules. It can be utilized as both a coating in slow-release formulations as well as a preservative to prevent color and taste changes. Pullulan also shows promise as a conjugate for vaccines and can be used as a blood plasma expander in place of dextran.

Pullulan finds use in the cosmetics industry because it is non-toxic and non-irritating to the human body. Eye cosmetics, lotions and shampoos, as well as powders, facial packs, hair dressings and tooth powders can all contain pullulan.

Pullulan can also be formed into fibers that resemble nylon or rayon. Pullulan that is compressed or extruded can be formed into materials that resemble polystyrene or polyvinyl alcohol. Pullulan also has applications in a wide variety of industries, from making paint and electronics components to paper production and use as a flocculating agent.

However, pullulan is expensive to make, despite its ecological benefits over petroleum products. One impediment to producing pullulan is the need to extract melanin and melanin-related pigments which contaminate cultures of *A. pullulans*. Thus, one object of the present invention is to provide *A. pullulans* strains that make pullulan more economically feasible by, for example, bypassing the step of removing melanin, which adds extra time and expense to the pullulan production process.

In one embodiment, the present invention provides a method of producing melanin-free pullulan directly in cultures of *A. pullulans*. This embodiment can be achieved by utilizing a strain lacking a functional PKS gene. In a particular embodiment, production of melanin-free pullulan directly in a culture is achieved using a strain specifically disclosed in the Examples section below.

*Massoia* Lactone

*Massoia* lactone is an alkyl lactone derived from the bark of the *Massoia* tree (*Cryptocaria massoia*) found in Papua, Indonesia. *Massoia* lactone is a popular natural coconut flavoring ingredient, but harvesting and extracting this compound from the bark of the *Massoia* tree is an expensive process that results in death of the tree. Consequently, most *massoia* lactone is synthetically produced from petroleum-based precursors, despite consumer and producer preferences for natural products (Harbindu and Kumar, *Synthesis* (12):1954-59 (2011). Prior to construction of the PksKO strain described herein, there has never been a report or other description of a *massoia*-lactone-producing strain of *A. pullulans*. Thus, we describe herein an invention allowing the production of *massoia* lactone by *A. pullulans*. *A. pullulans* represents a potential alternative source of *massoia* lactone that is natural, renewable, and environmentally friendly. In addition, we anticipate that the market size of *massoia* lactone could increase significantly if we are able to reduce the cost through fermentative production. In addition, there may be other potential applications of using *massoia* as an anti-bitter agent for artificial sweeteners (Putter and Wonschik, PCT Pub. No. WO2013079187) and also an oxygenate fuel additive (Robinson, US. Pub. No. US20060096158A1).

Production of *massoia* lactone by *Aureobasidium* species, including *A. pullulans*, has not been previously described. Thus, one embodiment of the present invention is a *massoia*-lactone-producing strain of *A. pullulans*. Another embodiment of the present invention is a strain of *A. pullulans* that lacks a functional PKS gene. Still another embodiment of the present invention is a *massoia*-lactone-producing strain of *A. pullulans* that lacks a functional PKS gene and also lacks one or more of: a functional MPD1 gene, a functional MDH2 gene, and a functional MDH1 gene.

Other Bioproducts

One of skill in the art will recognize that the strains of *A. pullulans* described herein can be used to produce a bioproduct of interest. In some embodiments, the bioproduct produced utilizing the strains and methods of the present invention is a liamocin, pullulan or *massoia* lactone. In other embodiments, the bioproduct produced utilizing the strains and methods of the present invention is poly (β-malic acid), β-glucan, aureobasidin, a lactone, an intracellular fatty acid or triacylglycerol. In still other embodiments, a strain of *A. pullulans* that lacks a functional PKS gene and is grown under conditions sufficient to produce one or more melanin-free bioproducts, including but not limited to a liamocin, pullulan, *massoia* lactone and other lactones, poly (β-malic acid), β-glucan, aureobasidin, an intracellular fatty acid and triacylglycerol.

Products

The present invention further provides a medicament, nutritional or pharmaceutical composition comprising any of the bioproducts produced by a genetically altered strain of the present invention. These compositions can be administered in various ways suitable for therapy and can be administered alone or as an active ingredient in combination with pharmaceutically acceptable carriers, diluents, adjuvants, and vehicles. Conventional methods such as administering the compounds as tablets, suspensions, solutions, emulsions, capsules, powders, syrups, and the like are usable. Known techniques to deliver the compositions orally or intravenously and retain biological activity are preferred. Formulations that can be administered subcutaneously, topically, or parenterally or intrathecal and infusion techniques are also contemplated by the present invention as well as suppositories and implants.

Pharmaceutically acceptable carriers, diluents, adjuvants and vehicles as well as implant carriers generally refer to inert, non-toxic solid or liquid fillers, diluents, or encapsulating material not reacting with the active ingredients of the invention. The pharmaceutical formulations suitable for injection include sterile aqueous solutions or dispersions and sterile powders for reconstitution into sterile injectable solutions or dispersions. The carrier can be a solvent or dispersing medium containing for example, water, ethanol, polyol such as glycerol propylene glycol, liquid polyethylene glycol, etc., and suitable mixtures thereof and vegetable oils.

Proper fluidity can be maintained by the use of a coating such as lecithin, by the maintenance of the required particle size in the case of dispersion and by the use of surfactants. Nonaqueous vehicles such as cottonseed oil, sesame oil, olive oil, soybean oil, corn oil, sunflower oil, or peanut oil and esters, such as isopropyl myristate, may also be used as solvents for compound compositions. Additionally various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, etc. It may be desirable to include isotonic agents, for example sugars, sodium chloride, etc. Prolonged absorption of the injectable pharmaceutical form can be brought about by the use of agents delaying absorption, for example, aluminum monostearate, gelatin, etc. Any vehicle, diluents or additive used would have to be compatible with the anti-microbial adhesion fraction A6 of the invention. The choice of delivery system is well within the ordinary skill in the art.

Having described the invention in general, below are examples illustrating the generation and efficacy of the invention. Neither the examples, nor the general description above should be construed as limiting the scope of the invention.

EXAMPLES

Example 1

A hygromycin expression cassette used in these transformations was constructed by fusing an *A. pullulans* translation elongation factor (TEF) promoter to an *Escherichi coli* hygromycin phosphotransferase gene. This was accomplished by PCR amplification of the TEF promoter using degenerate oligonucleotides ApTEF-F and ApTEF-R (Table 1); and *A. pullulans* NRRL 50383 (RSU6) DNA as template. The product was then cloned into pCR2.1 (Invitrogen) and further modified by PCR amplification with primers ApTEF-SalI and ApTEF-EcoRV in order to introduce restriction endonuclease sites. Plasmid pCSN43 was also modified by removing the 0.3 kb XbaI fragment and re-ligating the remaining 5.0 kb plasmid in order to shorten the *A. nidulans* TrpC terminator and remove an adjacent ClaI site within the polylinker. The *A. nidulans* TrpC promoter was then removed from this resultant plasmid by cutting with ClaI, blunting the restriction endonuclease overhangs, and then digesting with SalI. This linear fragment was then ligated to the modified TEF promoter fragment digested with SalI and EcoV. Lastly, this modified plasmid was used as template for PCR amplification with primers TEF-Hyg-P1 and TEF-Hyg-P2. This 2.5 kb hygromycin resistance cassette was used for all further plasmid constructs.

TABLE 1

Primers

| Primer name | Sequence 5'→3' | SEQ ID NO. |
|---|---|---|
| ApTEF-F ( | GGCTAGRYGCRCGAYTATYCAC | 8 |
| ApTEF-R | GTTGACGGTKRTGTATGGAAG | 9 |
| ApTEF-SalI | GCAGGTCGACGGCTAGGCGCGCGATTATTC | 10 |
| ApTEF-EcoRV | GCAGGATATCTTGACGGTTGTGTATGGAAGATTGAG | 11 |
| TEF-Hyg-P1 | CGGCTAGGCGCGCGATTATTC | 12 |
| TEF-Hyg-P2 | CGGCCGGCGTATTGGGTGTTA | 13 |
| pUC18-P1 | CGTAATCATGGTCATAGCTGTTTCC | 14 |
| pUC18-P2 | GCACTGGCCGTCGTTTTACAA | 15 |
| Mpd-P1Gib | GTCACGACGTTGTAAAACGACGGCCAGTGCGACCCGCCGCTCTTTGACCTACAG | 16 |
| Mpd-P2Gib | GCTGTGAATAATCGCGCGCCTAGCCGGGAGGGGAACAAAGCCATCACACC | 17 |
| Mpd-P3Gib | GCTCCGTAACACCCAATACGCCGGCCGGCGTGTCGGTCGTGCTCCTCTC | 18 |
| Mpd-P4Gib | CACACAGGAAACAGCTATGACCATGATTACGTTGTGGGCTTTGGAATCTGTGGA | 19 |
| Mpd-P5 | GCGGCAACATCGGTCGTGG | 20 |
| Mpd-P6 | CATTCCTTGCCGCGGTTGTAG | 21 |
| Mpd-P7 | TCAAGCGCCAAGGTTATCGGTCTG | 22 |
| Hyg-P11 | GCCGCTTTCCCTCCCATTCC | 23 |
| Mpd-P8 | GTGGCGACGATGGAGGCTTCT | 24 |
| Hyg-P13 | AGCCCCTGGGTTCGCAAAGATAAT | 25 |
| PKS4-P1Gib | GTCACGACGTTGTAAAACGACGGCCAGTGCGGCTTTGGGCGCATACCGAGAG | 26 |

TABLE 1 -continued

Primers

| Primer name | Sequence 5'→3' | SEQ ID NO. |
|---|---|---|
| PKS4-P2Gib | GCTGTGAATAATCGCGCGCCTAGCCGGCTGAAGGCCAGCACATCCAACT | 27 |
| PKS4-P3Gib | GCTCCGTAACACCCAATACGCCGGCCGGTCGGCCAGCGCATCCTCGTAT | 28 |
| PKS4-P4Gib | CACACAGGAAACAGCTATGACCATGATTACGGCTTCCTCCTGCTGCCAACACTC | 29 |
| PKS4-P5 | TCAGGGCCGATGTTAGGGATGCT | 30 |
| Hyg-P10 | TCGGCAGGATATCTTGACGGTTGT | 31 |
| PKS4-P6 | GTCCCGCCGGCTGTAAGGTG | 32 |
| Hyg-P13 | AGCCCCTGGGTTCGCAAAGATAAT | 33 |
| PKS4-P7 | GCGAGCGAGAGCGACCTGGAT | 34 |
| PKS4-P8 | ACAACTTCTCCGCTGCTGGTGGTAA | 35 |
| PKS4-P1 | GGCTTTGGGCGCATACCGAGAG | 36 |
| PKS4-P4 | GCTTCCTCCTGCTGCCAACACTC | 37 |
| MPD1-P1 | GACCCGCCGCTCTTTGACCTACAG | 38 |
| MPD1-P4 | TTGTGGGGCTTTGGAATCTGTGGA | 39 |
| Hyg-P1 | AGCTGCGCCGATGGTTTCTACAA | 40 |
| Hyg-P2 | CTGGGGCGTCGGTTTCCACTATC | 41 |
| Ura3-P1Gib | GTCACGACGTTGTAAAACGACGGCCAGTGCCGCCGCGTGCTTCCGTAGA | 42 |
| Ura3-P5Gib | GGTGCGTTGATGGTGCTGATCCTCTTCCTGGATACATCGGCCGAACACAG | 43 |
| Ura3-P4Gib | CACACAGGAAACAGCTATGACCATGATTACGGTAGGCGTATGCTGGTGGTGTTGG | 44 |
| Ura3-P6Gib | GGAAGAGGATCAGCACCATCAACGCACCGAGCAGCGCGGGTAATTTGATGAC | 45 |
| Ura3-P1 | CGCCGCGTGCTTCCGTAGA | 46 |
| Ura3-P4 | GTAGGCGTATGCTGGTGGTGTTGG | 47 |
| Ura3-P7 | TGGGGTGAGGGAAAGAGAAGGACA | 48 |
| Ura3-P8 | CGCTCAAAGGGCAAACATCAAAGA | 49 |
| Mdh1-P1Gib | GTCACGACGTTGTAAAACGACGGCCAGTGCTGCGGAGCCAACACCCAGATAG | 50 |
| Mdh1-P2Gib | GAACTTGTCCTTCTCTTTCCCTCACCCCAGGAAGCCACCGACACCAATGTG | 51 |
| Mdh1-P3Gib | GGATCTTTGATGTTTGCCCTTTGAGCGACTTCCGCCGTCTCTGTTTCGTC | 52 |
| Mdh1-P4Gib | CACACAGGAAACAGCTATGACCATGATTACGGAGGCTGAGGACAAGGCAAGAGAT | 53 |
| Mdh1-P1 | TGCGGAGCCAACACCCAGATAG | 54 |
| Ura3-P13 | CACGGCGGTATTGAGCGAGGTAA | 55 |
| Mdh-P4 | GAGGCTGAGGACAAGGCAAGAGAT | 56 |
| Ura3-P15 | GCCGCAAAGCAGACGAACCT | 57 |
| Mdh2-P1Gib | GTCACGACGTTGTAAAACGACGGCCAGTGCGAGTGGGCGGAGTTGGCGATAG | 58 |

TABLE 1 -continued

Primers

| Primer name | Sequence 5'→3' | SEQ ID NO. |
|---|---|---|
| Mdh2-P2Gib | GAACTTGTCCTTCTCTTTCCCTCACCCCAAGCGGCCTCAATACC CATACCAC | 59 |
| Mdh2-P3Gib | GGATCTTTGATGTTTGCCCTTTGAGCGCTCTGACGCCTCCACCT ACACCAC | 60 |
| Mdh2-P4Gib | CACACAGGAAACAGCTATGACCATGATTACGTTCACCCTTCGC CCAAACTGC | 61 |
| Mdh2-P1 | GAGTGGGCGGAGTTGGCGATAG | 62 |
| Mdh2-P2 | TTCACCCTTCGCCCAAACTGC | 63 |

Example 2

MPD1 Disruption Cassette/Strain Construction

Figure 3:
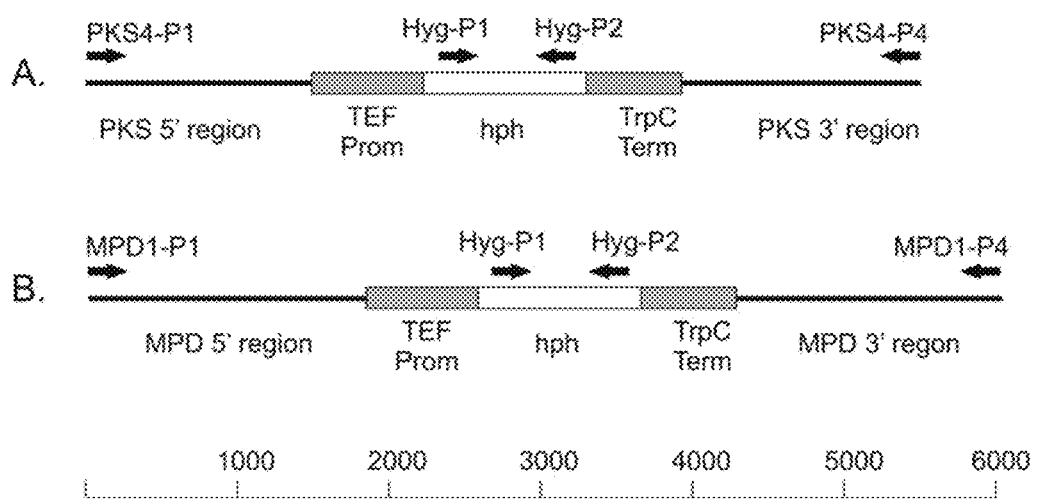
FIG. 3 provides a diagram of DNA constructs used for deletion of the (A) pks4 gene and (B) the mpd1 gene in *A. pullulans*. The *A. pullulans* trans elongation factor promoter (TEF Prom) was fused to the *Escherichia coli* hygromycin phosphotransferase gene (hph), and the TrypC terminator from *Aspergillus nidulans* (TrpC Term) obtained from plasmid pCSN43 (www.fgsc.net/fgn41/carroll.html). The hygromycin resistant expression cassette was then flanked with 5' upstream and 3' downstream regions of either the pks4 or mpd1 genes. Primers used for PCR amplification of DNA fragments are shown with arrows designating the direction of synthesis. Size of the constructs (base pairs) used in our examples is shown at the bottom.

A MPD1 (SEQ ID NO. 1) disruption plasmid was constructed by Gibson assembly using the following PCR fragments: (1) pUC18 amplified with primers pUC18-P1 and pUC18-P1, (2) MPD1 5' region amplified with primers MPD-P1Gib and MPD-P2Gib, (3) MPD1 3' region amplified with primers MPD-P3Gib and MPD-P4Gib, and (4) the 2.5 kb hygromycin resistance cassette previously amplified with primers TEF-Hyg-P1 and TEF-Hyg-P2 (FIG. 3) (See, Table 1 for primer sequences). The resultant plasmid served as template for PCR amplification of the overlapping split marker regions using primer combinations, a) MPD1-P1 and Hyg-P2; and b) MPD1-P4 and Hyg-P1. The resulting PCR product formed the MPD knockout cassette (SEQ ID NO. 6). The DNA fragments were purified by column separation or ethanol precipitation; and then used in equimolar amounts for transformation of A. pullulans NRRL 50384. Transformation was carried using electroporation as previously described (Varma, et al., Infect. Immun., 60(3):1101-8 (1992)) using logarithmically growing cells. After electroporation, cells were recovered for 3 hr in YPD medium (1% YE, 2% peptone, 2% glucose) prior to plating on YPD-Hyg plates containing 100 µg/ml hygromycin B.

Isolates were transferred at least two times on YPD-Hyg plates and then screened by PCR amplification to confirm the following integration patterns: (1) deletion of the native mpd1 gene using primers Mpd-P5 and Mpd-P6, (2) 5' cross-over integration of the transforming DNA using Mpd-P7 and Hyg-P11, and (3) 3' cross-over integration of the transforming DNA using Mpd-P8 and Hyg P13 (See, Table 1 for primer sequences). Primers Mpd-P7 and Mpd-P8 both anneal outside of the homologous regions of the transforming DNA so PCR amplification as described is persuasive evidence of gene replacement as designed.

Example 3

Figure 2:
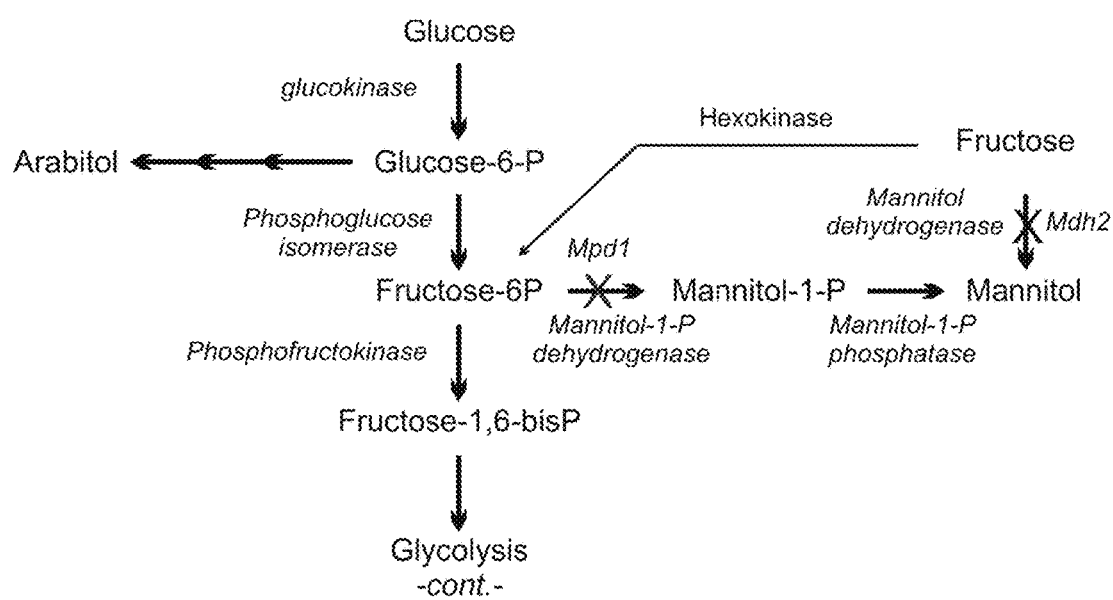
FIG. 2 provides a proposed biosynthetic pathway for production of mannitol and arabitol in *A. pullulans*.

The isolated MPD1 knock-out (MpdKO) transformants and parent strain A. pullulans NRRL 50384 were grown overnight in complex medium supplemented with either 50 g/L glucose or 50 g/L fructose. Cells were then harvested, lysed by shaking with 0.5 mM zirconia/glass beads, and centrifuged to produce cell-free lysate. These lysates were then analyzed for mannitol, arabitol, glycerol, and trehalose content by HPCL using an Aminex HPX-87H column and refractive index for detection. All polyol and trehalose concentrations were normalized against the protein content to normalize for discrepancies in lysis efficiency. The MpdKO strain produced approximately 12× less intracellular mannitol compared with A. pullulans NRRL 50384 when grown on glucose. The results are shown in Table 2, where standard deviations are in parentheses and values with statistically different values compared with NRRL 50384 controls grown under the same condition are marked with asterisks ($p<0.05$ with T-Test). Under these same conditions, there was almost a 2-fold increase in glycerol and 35% increase in trehalose for the MpdKO strain compared with the parent isolate. However, there was not any statistical difference in the amount of intracellular arabitol with this group. When this same strain were grown with fructose, there was not any statistical difference for the intracellular polyols and trehalose between the NRRL 50384 and MpdKO strain, but there were large differences in relative amounts compared with NRRL 50384 grown in glucose. Most notable was the 4-fold increase in mannitol for NRRL 50384 when grown in fructose containing medium. It is assumed the increased mannitol is due to fructose being converted directly into mannitol through a Mdh2-mediated reaction. This reaction would explain why the MpdKO strain did not exhibit decreased mannitol when grown with fructose, since Mpd1 protein would not be involved in this pathway (FIG. 2).

TABLE 2

Polyol and Trehalose Accumulation in WT and MpdKO strains.

| Strain/carbon source | Relative intracellular concentrations | | | |
|---|---|---|---|---|
| | Mannitol | Arabitol | Glycerol | Trehalose |
| 50384/glucose | 0.660 (0.020) | 0.127 (0.021) | 0.062 (0.001) | 2.070 (0.022) |
| MpdKO/glucose | 0.055 (0.014)* | 0.109 (0.011) | 0.112 (0.015)* | 2.801 (0.156)* |
| 50384/Fructose | 2.768 (0.046) | 0.012 (0.021) | 0.038 (0.016) | 0.323 (0.008) |
| MpdKO/fructose | 2.7196 (0.107) | 0.028 (0.010) | 0.028 (0.010) | 0.323 (0.010) |

Example 4

MpdKO Strain, Liamocin Analysis

Figure 4:
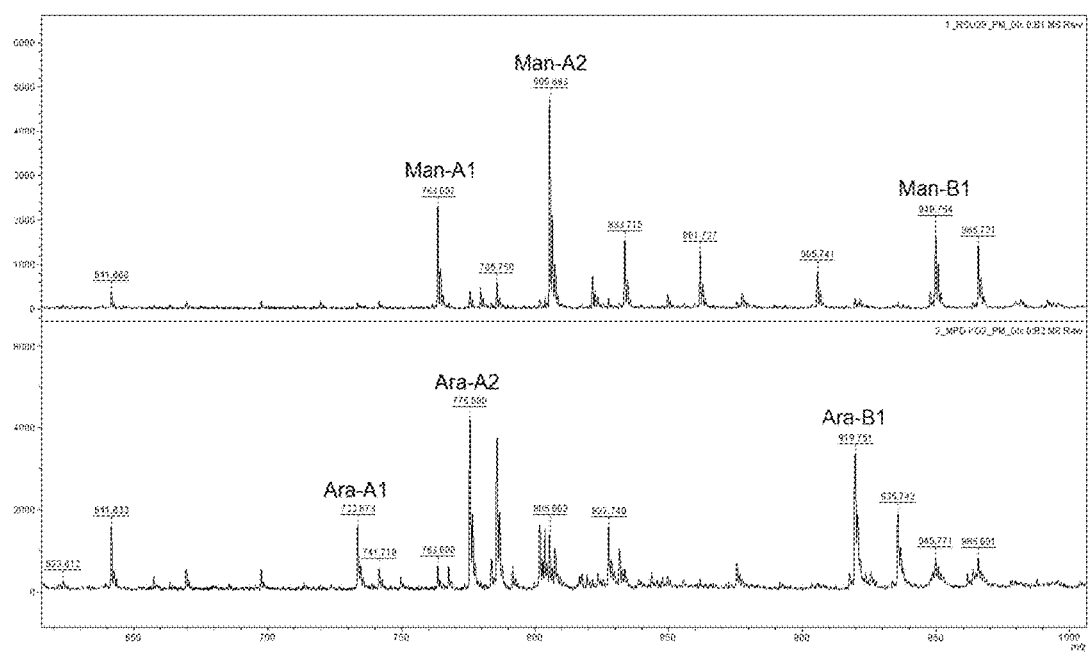
FIG. 4 provides MALDI-TOF spectra of purified liamocins from *A. pullulans* NRRL 50384 (top) and *A. pullulans* MpdKO transformant grown on PM medium with 50 g/L glucose.
Figure 5:
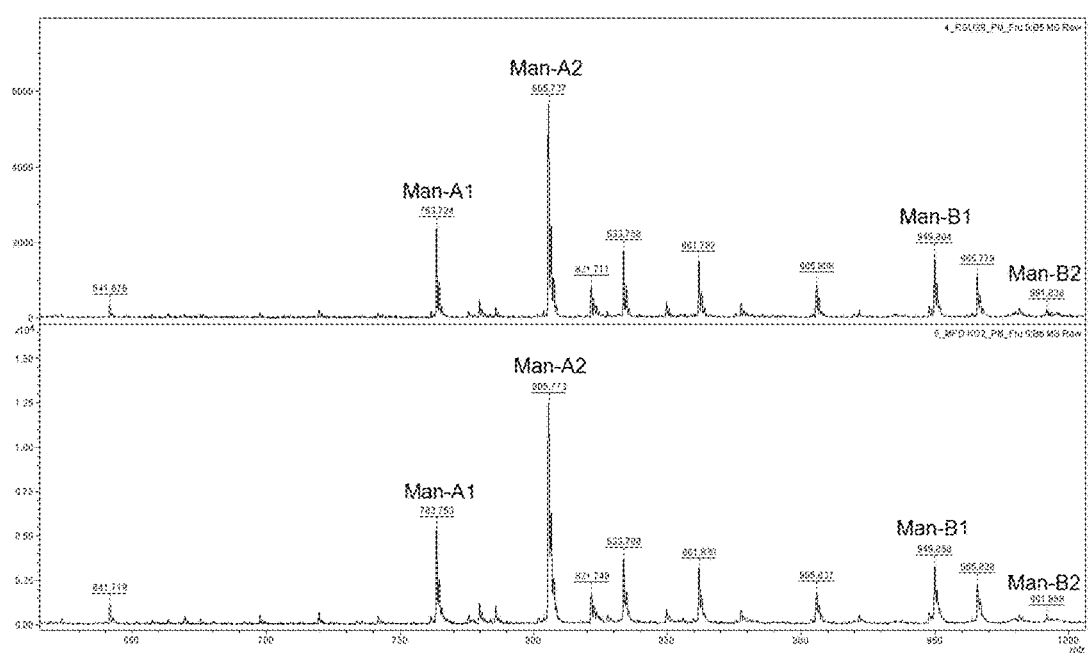
FIG. 5 provides MALDI-TOF spectra of purified liamocins from *A. pullulans* NRRL 50384 (top) and *A pullulans* MpdKO transformant grown on PM medium with 50 g/L fructose.

To analyze whether deletion of the MPD1 gene shifted bioproduct production in genetically altered *A. pullulans* strains, liamocins were produced and purified as previously described (Manitchotpisit, 2011, ibid.) from cultures grown with 50 g/L glucose, the MpdKO strain produced nearly 100% arabitol-containing liamocins compared to 100% mannitol-containing liamocins for NRRL 50384 (FIG. 4). Under these conditions, there was only a 15% decrease in yield compared with the wildtype, demonstrating that the robustness and productivity of this strain were minimally affected. When grown with 50 g/L fructose, there was not any statistical difference in liamocin yield and molecular structures between the parent and MpdKO strains (FIG. 5). It is assumed that the formation of mannitol-containing liamocins under these conditions is a result of the high amount of mannitol, presumably from mannitol dehydrogenase (the protein encoded by MDH2) conversion of fructose, and the relatively lower amount of arabitol.

Example 5

PKS Disruption Cassette/Strain Construction

A PKS4 disruption plasmid was constructed by Gibson assembly using the following PCR fragments: (1) pUC18 amplified with primers pUC18-P1 and pUC18-P1, (2) PKS4 5' region amplified with primers PKS4-P1Gib and PKS4-P2Gib, (3) PKS4 3' region amplified with primers PKS4-P3Gib and PKS4-P4Gib, and (4) the 2.5 kb hygromycin resistance cassette previously amplified with primers TEF-Hyg-P1 and TEF-Hyg-P2 (FIG. 3) (See, Table 1 for primer sequences). The resultant plasmid served as template for PCR amplification of the overlapping split marker regions using primer combinations, a) PKS4-P1 and Hyg-P2; and b) PKS4-P4 and Hyg-P1 (See, Table 1 for primer sequences). The resulting PCR product formed the PKS knockout cassette (SEQ ID NO. 7). The DNA fragments were purified by column separation or ethanol precipitation; and then used in equimolar amounts for transformation of *A. pullulans* NRRL 50384. Transformation was carried using electroporation as previously described (Varma, et al., *Infect. Immun.*, 60(3): 1101-8 (1992)) using logarithmically growing cells. After electroporation, cells were recovered for 3 hr in YPD medium (1% YE, 2% peptone, 2% glucose) prior to plating on YPD-Hyg plates containing 100 m/ml hygromycin B.

Isolates were transferred at least two times on YPD-Hyg plates and then screened by PCR amplification to confirm the following integration patterns: (1) 5' cross-over integration of the transforming DNA using PKS4-P5 and Hyg-P10, (2) 3' cross-over integration of the transforming DNA using PKS4-P6 and Hyg P13, and (3) deletion of the native pks4 gene using primers PKS4-P7 and PKS4-P8 (See, Table 1 for primer sequences). Primers PKS4-P5 and PKS4-P6 both anneal outside of the homologous regions of the transforming DNA so PCR amplification as described is persuasive evidence of gene replacement as designed.

Isolates were transferred at least two times on selective medium and then screened for PCR amplification of the 5' and 3' integration junctions; and deletion of the native gene, which would only occur with integration of the constructed DNA fragment. Confirmed deletion isolates were chosen for further analyses. The resulting strain lacking a functional PKS4 gene was termed PksKO.

Example 6

Figure 6:
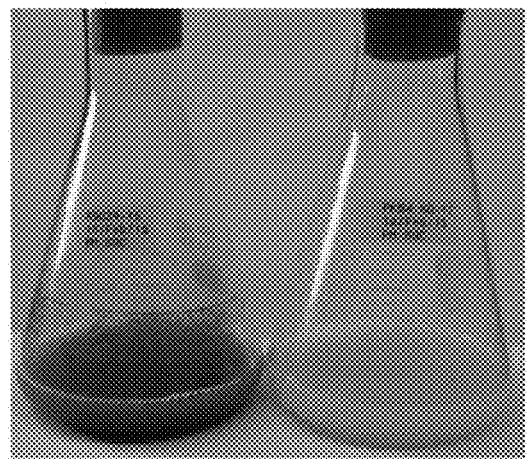
FIG. 6 provides a comparison of melanin pigments between cultures of *A. pullulans* NRRL 50384 (left) and *A. pullulans* PksKO transformant (right).
Figure 7:
FIG. 7 provides a comparison of pigments in liamocins purified from *A. pullulans* NRRL 50384 (left) and *A. pullulans* PksKO transformant (right).
Figure 8:
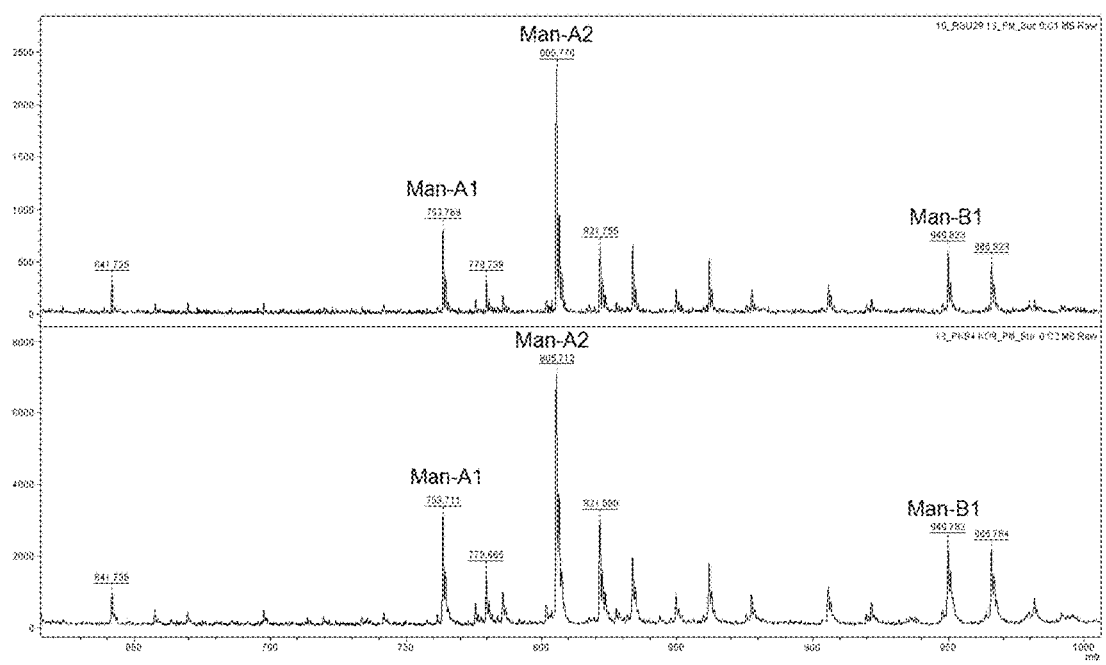
FIG. 8 provides MALDI-TOF spectra of purified liamocins from *A. pullulans* NRRL 50384 (top) and *A. pullulans* PksKO transformant.

To determine whether a PksKO strain was capable of producing a desired bioproduct (liamocins) without melanin contamination, liamocins were produced and purified as previously described (Manitchotpisit, 2011, ibid.). NRRL 50384 and PksKO strains were utilized for this analysis. Cultures were grown with 50 g/L sucrose, the isolated knock-out (KO) transformant had no melanin-pigment accumulation in the cultures (FIG. 6) and the final product had superior clarity (FIG. 7). There was not any statistical difference in liamocin yield (data not shown) and the molecular structures (FIG. 8) were the same between the parent and KO strains.

Example 7

Deleting multiple genes in *A. pullulans* is more convenient with the availability of multiple selectable markers, so we created a ura3 auxotroph in *A. pullulans*. Using the sequenced genome of *A. pullulans* NRRL 50384, we identified an orotidine 5'phosphate decarboxylase gene that was homologus to another previously described ura3 gene. A Ura3 disruption plasmid was constructed by Gibson assembly using the following PCR fragments: (1) pUC18 amplified with primers pUC18-P1 and pUC18-P1, (2) Ura3 5' region amplified with primers Ura3-P1Gib and Ura3-P5Gib using *A. pullulans* NRRL 50384 DNA as template, and (3) Ura3 3' region amplified with primers Ura3-P4Gib and Ura4-P6Gib using *A. pullulans* NRRL 50384 DNA as template. The resultant plasmid served as a template for PCR amplification using primers Ura3-P1 and Ura3-P4. The DNA fragment were purified by column separation or ethanol precipitation; and then used for transformation of *A. pullulans* NRRL 50384. Transformation was carried using electroporation as previously described using logarithmically growing cells. After electroporation, cells were transferred to yeast nitrogen base without amino acids (YNB, Difco) supplemented with 2% glucose and 50 mg/L uracil, and 1 mg/ml 5-fluoroorotic (FOA) acid for selection of uracil auxotrophs. Isolates were transferred at least two times on YNB-FOA plates and then screened on YNB with and without uracil. All of the recovered isolates were confirmed uracil auxotrophs with mutations in the ura3 gene. We further established that at least one of the isolates, *A. pullulans* B44p41-01, could be restored to uracil prototrophy by transformation with a ura3 DNA fragment obtained from PCR amplification using primers Ura3-P7 and Ura-P8.

Example 8

Using the sequenced genome of *A. pullulans* NRRL 50384, we identified two MDH genes that are likely involved in conversion between mannitol and fructose. We deleted the first of these genes, termed "MDH1". A MDH1 disruption plasmid was constructed by Gibson assembly using the following PCR fragments: (1) pUC18 was amplified with primers pUC18-P1 and pUC18-P1, (2) MDH1 5' region was amplified with primers Mdh1-P1Gib and Mdh1-P2Gib, (3) MDH1 3' region was amplified with primers Mdh1-P3Gib and Mdh1-P4Gib, and (4) the 2.5 kb ura3 cassette previously amplified with primers Ura3-P7 and Ura3-P8 (See, Table 1 for primer sequences). The resultant plasmid served as template for PCR amplification of the overlapping split marker regions using primer combinations, a) Mdh1-P1 and Ura3-P13; and b) Mdh1-P4 and Ura3-P15 (See, Table 1 for primer sequences). The DNA fragments were purified by column separation or ethanol precipitation; and then used in equimolar amounts for transformation of *A. pullulans* NRRL 50384. Transformants with confirmed integration and deletion of the mdh1 gene, as indicated by PCR amplification, were then used as a recipient strain for transformation with the overlapping MPD1-Hyg fragments as described above. Resulting knockout strains were analyzed for intracellular polyols, as previously described. The results show that neither *A. pullulans* (mdh1) nor *A. pullulans* (mdh1, mpd1) had significant differences in intracellular mannitol, arabitol, glycerol, and trehalose compared with *A. pullulans* NRRL 50384. However, both mdh1 deletion strains were incapable of growth in YNB (2% mannitol), while *A. pullulans* NRRL 50384 and *A. pullulans* (mpd1) were able to achieve $OD_{600}$>8.0 after 48 hrs.

Example 9

Deletion of the second putative MDH-encoding gene (termed "MDH2") that was identified can be achieved using the same scheme as outlined above. The resulting strain is termed Mdh2KO. A MDH2 disruption plasmid is constructed by Gibson assembly using the following PCR fragments: (1) pUC18 amplified with primers pUC18-P1 and pUC18-P1, (2) MDH2 5' region amplified with primers Mdh2-P1Gib and Mdh2-P2Gib, (3) MDH2 3' region amplified with primers Mdh2-P3Gib and Mdh2-P4Gib, and (4) the 2.5 kb ura3 cassette previously amplified with primers Ura3-P7 and Ura3-P8 (See, Table 1 for primer sequences). The resultant plasmid serves as template for PCR amplification of the overlapping split marker regions using primer combinations, a) Mdh2-P1 and Ura3-P13; and b) Mdh2-P4 and Ura3-P15. The DNA fragments are purified by column separation or ethanol precipitation; and then used in equimolar amounts for transformation of *A. pullulans* NRRL 50384.

To analyze whether deletion of the MDH2 gene shifted bioproduct production in genetically altered *A. pullulans* strains, liamocins are produced, purified and analyzed as previously described (Manitchotpisit, 2011, ibid.). Transformant *A. pullulans* (mdh2) served as a recipient strain for further deletion of mpd1 as described in Example 2. Cultures of *A. pullulans* (mdh2), *A. pullulans* (mdh2, mpd1) and *A. pullulans* NRRL 50384 were grown in the presence of 50 g/L glucose or 50 g/L fructose and differences in intracellular mannitol, arabitol, glycerol, trehalose, and fructose are analyzed as described in Example 3, but are expressed based on cell dry weight in Table 3, where standard deviations are in parentheses and quantities with statistically different values compared with NRRL 50384 controls grown under the same conditions are marked with asterisks (p<0.05 with T-Test).

TABLE 3

Polyol and fructose accumulation in WT, Mdh2KO, and Mdh2.Mpd1KO strains

| Strain/carbon source | Intracellular concentrations (µg/mg cell dry weight) | | | | |
|---|---|---|---|---|---|
| | Mannitol | Arabitol | Glycerol | Trehalose | Fructose |
| 50384/glucose | 67.1 (5.3) | 5.0 (0.9) | 2.7 (0.1) | 125.7 (6.5) | 0 |
| Mdh2KO/glucose | 66.9 (3.9) | 3.8 (0.1) | 2.7 (0.1) | 117.0 (2.5) | 0 |
| Mdh2KO/Mpd1KO/glucose | 0* | 3.0 (0.4) | 5.8 (0.2)* | 181.7 (8.8)* | 0 |
| 50384/fructose | 147.8 (8.4) | 0.7 (1.0) | 2.0 (0.6) | 17.2 (0.8) | 80.8 (26.3) |
| Mdh2KO/fructose | 102.2 (3.5)* | 0.5 (0.0) | 3.3 (0.1) | 54.6 (2.7)* | 37.9 (3.2) |
| Mdh2KO/Mpd1KO/fructose | 6.1 (0.2)* | 1.7 (0.1)* | 6.8 (0.1)* | 99.6 (1.8)* | 61.0 (1.5) |

There was not any significant decrease in mannitol for the Mdh2KO strain compared with the parent isolate when grown on glucose. However, the Mdh2KO/Mpd1KO strain did not have any detectable mannitol under these same conditions. Arabitol was only slightly less for the two modified strains, but the Mdh2KO/Mpd1KO strain had more than 2-fold increase in glycerol and nearly 50% increase in trehalose compared with the parent strain. The Mdh2KO strain did not show any difference in the levels of these compounds compared with the parent strain under these conditions.

When grown on fructose, there was a slight decrease in the mannitol for the Mdh2KO strain compared with the parent isolate, while the Mdh2KO/Mpd1KO strain had more than 95% less mannitol compared with the control. Under these same conditions, the Mdh2KO/Mpd1KO strain also had significantly higher concentrations of arabitol, glycerol, and trehalose compared with the parent strain. The Mdh2KO strain had significantly higher trehalose compared with the control.

Figure 10:
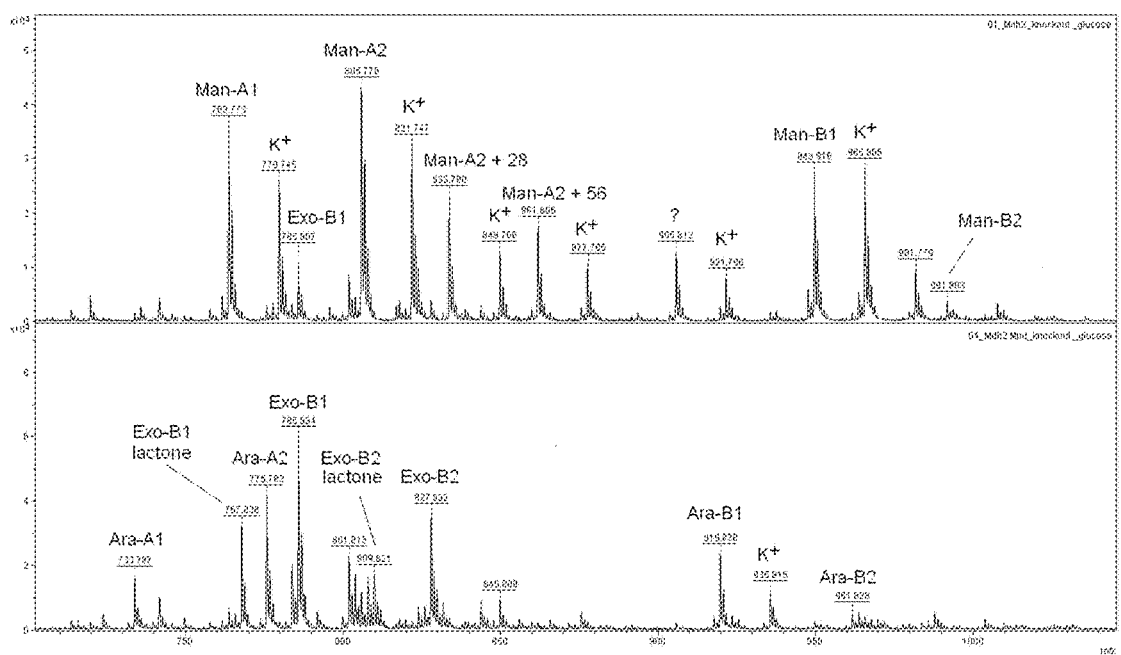
FIG. 10 provides MALDI-TOF spectra of purified liamocins from *A. pullulans* Mdh2KO transformant (top) and *A. pullulans* Mdh2KO/Mpd1KO transformant grown on PM medium with 50 g/L glucose.
Figure 11:
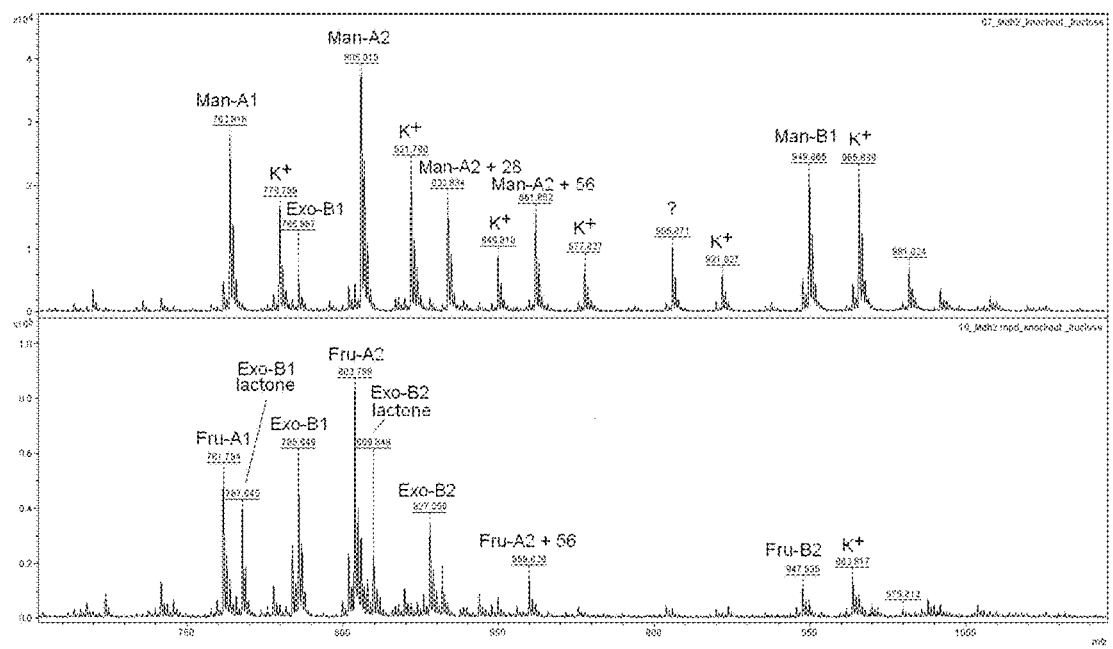
FIG. 11 provides MALDI-TOF spectra of purified liamocins from *A. pullulans* Mdh2KO transformant (top) and *A. pullulans* Mdh2KO/Mpd1KO transformant grown on PM medium with 50 g/L fructose.
Figure 12:
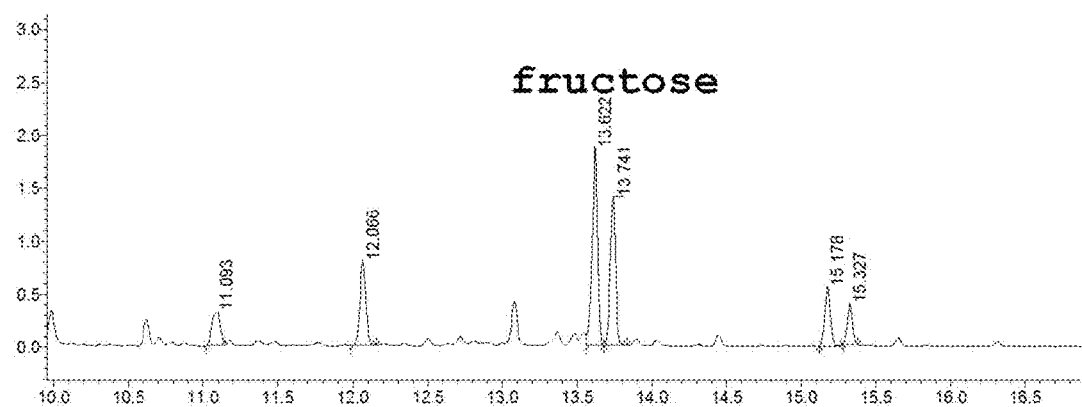
FIG. 12 provides GC profiles (as peracetates) of purified and treated liamocins from *A. pullulans* Mdh2.Mpd1KO transformant grown on PM medium with 50 g/L fructose.

Further analysis of these cultures revealed that the Mdh2KO strain produced nearly 100% mannitol-containing liamocin (FIGS. 10 and 11) with both glucose and fructose in a similar manner as the parent strain (FIGS. 4 and 5). The Mdh2KO/Mpd1KO strain produced significant amounts of arabitol-containing liamocin with glucose (FIG. 10), but exophilins (i.e., liamocin without a polyol or carbohydrate headgroup) appeared to be the predominant structure under these conditions. The Mdh2KO/Mpd1KO strain grown with fructose also appeared to have a predominance of exophilins, but also contained significant amounts of a surprisingly unique structure containing fructose as a headgroup (FIG. 11). The assignment of the fructose head group was further confirmed by hydrolyzing liamocin samples using 2M TFA (80° C., 1 hr), partitioning with aqueous chloroform to remove the released fatty acids, and peracetylating the released fructose in the aqueous layer (using acetic anhydride, pyridine 1:1 v/v, 80° C., 30 min). The peracetylated headgroup components were analyzed by gas chromatography (FIG. 12), and the structural assignment of the peracetylated fructose was confirmed by GC/MS. The structure of these fructose-type liamocins has not been previously described and has never been observed to be formed by WT strains.

Example 10

Figure 9:
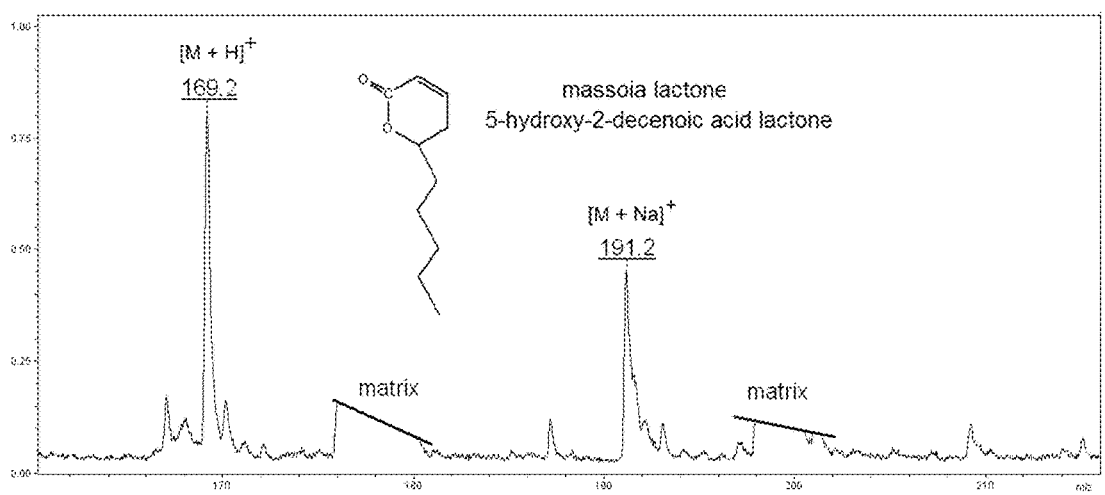
FIG. 9 provides a MALDI-TOF spectrum of purified *massoia* lactone from *A. pullulans* PksKO transformant.

As another example, we report on the simplified purification of *massoia* lactone from *A. pullulans* strain PksKO. In analyzing the PksKO strain, we discovered that this strain produced *massoia* lactone, a bioproduct never before identified as produced by *A. pullulans*. However, selective extraction of the cultures of the *Aureobasidium* PksKO strain with butan-2-one followed by butan-2-one:chloroform:water (1:2:2 by volume) partitioning recovered a product identical to *massoia* lactone (1H-NMR, 13C-NMR, COSY, HSQC, HMBC, and MALDI-TOF MS analyses. 13C-NMR chemical shifts (in CDCl3): C1 C=O, 165.46 ppm; C2 CH, 121.26 ppm; C3 CH, 145.61 ppm; C4 CH2, 29.36 ppm; C5 CH 78.31 ppm; C6 CH2, 34.76 ppm; C7 CH2, 24.45 ppm; C8 CH2, 31.50 ppm; C9 CH2, 22.47 ppm; C10 CH3, 13.94 ppm. M=m/z 168; [M=Na]+=m/z 191. The *massoia* lactone was of high purity (FIG. 9), and the NMR data was obtained without the need for chromatography clean-up. Determination of yield can be determined gravimetrically using *A. pullulans* PksKO. Purification of liamocins will be as previously described, followed by butan-2-one:chloroform:water (1:2:2 by volume) partitioning to recover *massoia* lactone.

What is claimed is:

1. A method of producing a melanin-free bioproduct from a culture of *Aureobasidium pullulans*, wherein said bioproduct is selected from the group consisting of: pullulan, a liamocin, a lactone, an exophilin, poly(β-malic acid), β-glucan, aureobasidin, an intracellular fatty acid, and a triacylglycerol comprising the steps of
   a) growing a culture of *A. pullulans* lacking a functional polyketide synthase (PKS4) gene under conditions sufficient to support the production of a bioproduct of interest; and
   b) collecting said bioproduct from at least part of said culture, thereby producing a melanin-free bioproduct.

2. The method of claim 1, wherein said bioproduct is pullulan.

3. The method of claim 1, wherein said bioproduct is a liamocin.

4. The method of claim 3, wherein said liamocin has a head group comprising lactose, glucose, mannose, galactose, arabinose, xylose, glucitol, galactitol, xylitol, ribitol, threitol, erythritol, or glycerol.

5. The method of claim 1, wherein the bioproduct is *massoia* lactone.

6. The method of claim 1, wherein said *A. pullulans* comprises strain NRRL 67080.

* * * * *